US010765634B2

(12) United States Patent
Little et al.

(10) Patent No.: US 10,765,634 B2
(45) Date of Patent: Sep. 8, 2020

(54) CONTROLLED RELEASE FORMULATIONS FOR THE INDUCTION AND PROLIFERATION OF BLOOD CELLS

(71) Applicant: University of Pittsburgh—Of the Commonwealth System of Higher Education, Pittsburgh, PA (US)

(72) Inventors: Steven R. Little, Allison Park, PA (US); Giorgio Raimondi, Pittsburgh, PA (US); Angus W. Thomson, Pittsburgh, PA (US); Siddharth Jhunjhunwala, Chennai (IN)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 451 days.

(21) Appl. No.: 14/372,977

(22) PCT Filed: Jan. 22, 2013

(86) PCT No.: PCT/US2013/022518
§ 371 (c)(1),
(2) Date: Jul. 17, 2014

(87) PCT Pub. No.: WO2013/112456
PCT Pub. Date: Aug. 1, 2013

(65) Prior Publication Data
US 2015/0079026 A1    Mar. 19, 2015

Related U.S. Application Data

(60) Provisional application No. 61/590,102, filed on Jan. 24, 2012.

(51) Int. Cl.
| | |
|---|---|
| A61K 45/00 | (2006.01) |
| A61K 47/00 | (2006.01) |
| A61K 9/16 | (2006.01) |
| A61K 31/436 | (2006.01) |
| A61K 31/203 | (2006.01) |
| A61K 38/22 | (2006.01) |
| A61K 38/18 | (2006.01) |
| A61K 38/20 | (2006.01) |
| A61K 39/00 | (2006.01) |

(52) U.S. Cl.
CPC ............ *A61K 9/16* (2013.01); *A61K 9/1635* (2013.01); *A61K 9/1641* (2013.01); *A61K 9/1647* (2013.01); *A61K 9/1658* (2013.01); *A61K 31/203* (2013.01); *A61K 31/436* (2013.01); *A61K 38/1841* (2013.01); *A61K 38/2013* (2013.01); *A61K 38/2278* (2013.01); *A61K 39/001* (2013.01); *A61K 39/0008* (2013.01)

(58) Field of Classification Search
None
See application file for complete search history.

(56) References Cited

U.S. PATENT DOCUMENTS

| | | | |
|---|---|---|---|
| 4,279,926 A | 7/1981 | Bruzzese et al. | 424/316 |
| 4,569,937 A | 2/1986 | Baker et al. | 514/282 |
| 4,587,252 A | 5/1986 | Arnold | 514/282 |
| 4,690,927 A | 9/1987 | Voss et al. | 514/282 |
| 4,844,907 A | 7/1989 | Elger et al. | 424/465 |
| 5,190,947 A | 3/1993 | Riess et al. | 514/282 |
| 5,200,558 A | 4/1993 | Kwan | 562/496 |
| 5,364,634 A | 11/1994 | Lew | 424/451 |
| 5,463,117 A | 10/1995 | Stroppolo et al. | 562/496 |
| 5,540,931 A * | 7/1996 | Hewitt | A61K 9/0014 424/434 |
| 6,005,005 A | 12/1999 | Stroppolo et al. | 514/565 |
| 6,727,286 B2 | 4/2004 | Pavliv | 514/565 |
| 2007/0275027 A1 * | 11/2007 | Wen | A61K 9/0024 424/422 |

FOREIGN PATENT DOCUMENTS

| | | | |
|---|---|---|---|
| WO | WO/2011/006029 | 1/1911 | |
| WO | WO/2011/031996 | 3/2011 | |
| WO | WO 2012054920 A2 * | 4/2012 | A61K 31/59 |

OTHER PUBLICATIONS

Maldonado et al., 2010, Adv. Immunol. vol. 108: 111-165.*
Chevalier et al., 2013, Blood. vol. 121: 29-37.*
Balasa et al., 2000, J. Immunol. vol. 165: 2841-2849.*

(Continued)

*Primary Examiner* — Amy E Juedes
(74) *Attorney, Agent, or Firm* — Baker Botts L.L.P.

(57) ABSTRACT

The absence of regulatory T cells (Treg) may underlie disorders including but not limited to autoimmunity, dermatitis, periodontitis and even transplant rejection. Enhancing local numbers of Treg through in situ Treg expansion or induction is contemplated herein as a treatment option for these disorders. Current methods for in vivo Treg expansion are not Treg specific and are associated with many adverse side-effects. The data presented herein provides in vitro testing of a Treg-inducing microparticle providing a predictable controlled release for combinations of cytokines and drugs (e.g., IL-2, TGF-β, and/or rapamycin) resulting in targeted Treg migration. These controlled release microparticles are also capable of inducing FoxP3+ Treg in human cells in vitro suggesting that these compositions be developed into an in vivo Treg induction and expansion therapy.

5 Claims, 20 Drawing Sheets

(56) References Cited

OTHER PUBLICATIONS

Bhaysar et al., 2008, Gene Ther. vol. 15: 1200-1209.*
Frangogiannis, 2017, J. Thorac. Dis. vol. 9: S52-S63.*
Zhang et al., 2010, J. Immunol. vol. 185: 4750-59.*
Sehrawat et al., 2008, J. Virol. vol. 82: 6838-6851.*
Anonymous. (2011) "Deal watch: Boosting TRegs to target autoimmune disease," *Nature Reviews Drug Discovery* 10(8), 566-566.
Benson, M. J. et al. (2007) "All-trans retinoic acid mediates enhanced T reg cell growth, differentiation, and gut homing in the face of high levels of co-stimulation," *Journal of Experimental Medicine* 204(8), 1765-1774.
Bettelli, E. et al. (2006) "Reciprocal developmental pathways for the generation of pathogenic effector TH17 and regulatory T cells," *Nature* 441(7090), 235-238.
Beyersdorf, N. et al. (2005) "Selective targeting of regulatory T cells with CD28 superagonists allows effective therapy of experimental autoimmune encephalomyelitis," *Journal of Experimental Medicine* 202(3), 445-455.
Bour-Jordan, H. et al. (2009) "Regulating the regulators: costimulatory signals control the homeostasis and function of regulatory T cells," *Immunological Reviews* 229(1), 41-66.
Bovenschen, H. J. et al. (2011) "Foxp3+ Regulatory T Cells of Psoriasis Patients Easily Differentiate into IL-17A-Producing Cells and Are Found in Lesional Skin," *Journal of Investigative Dermatology* 131(9), 1853-1860.
Brunstein, C. G. et al. (2011) "Alternative donor transplantation after reduced intensity conditioning: results of parallel phase 2 trials using partially HLA-mismatched related bone marrow or unrelated double umbilical cord blood grafts," *Blood* 118(2), 282-288.
Brunstein, C. G. et al. (2010) "Infusion of ex vivo expanded T regulatory cells in adults transplanted with umbilical cord blood: safety profile and detection kinetics," *Blood* 117(3), 1061-1070.
Brusko, T. M. et al. (2008) "Human regulatory T cells: role in autoimmune disease and therapeutic opportunities," *Immunological Reviews* 223(1), 371-390.
Campbell, D. J. et al. (2011) "Phenotypical and functional specialization of FOXP3+ regulatory T cells," *Nature Reviews Immunology* 11(2), 119-130.
Chen, W. et al. (2003) "Conversion of Peripheral CD4+CD25− Naive T Cells to CD4+CD25+ Regulatory T Cells by TGF-β Induction of Transcription Factor Foxp3," *Journal of Experimental Medicine* 198(12), 1875-1886.
Cobbold, S. P. et al. (2009) "Infectious tolerance via the consumption of essential amino acids and mTOR signaling," *Proceedings of the National Academy of Sciences* 106(29), 12055-12060.
Collison, L. et al. (2011) "In Vitro Treg Suppression Assays," in *Regulatory T Cells* (Kassiotis, G., et al., Eds.), pp. 21-37, Humana Press.
De Kleer, I. M. et al. (2004) "CD4+CD25bright Regulatory T Cells Actively Regulate Inflammation in the Joints of Patients with the Remitting Form of Juvenile Idiopathic Arthritis," *Journal of Immunology* 172(10), 6435-6443.
Defail, A. J. et al. (2006) "Controlled release of bioactive TGF-β1 from microspheres embedded within biodegradable hydrogels," *Biomaterials* 27(8), 1579-1585.
Delgado, M. et al. (2001) "Vasoactive intestinal peptide prevents experimental arthritis by downregulating both autoimmune and inflammatory components of the disease," *Nature Medicine* 7(5), 563-568.
Delgado, M. et al. (2004) "VIP/PACAP preferentially attract Th2 effectors through differential regulation of chemokine production by dendritic cells," *FASEB Journal*.
Depaolo, R. W. et al. (2011) "Co-adjuvant effects of retinoic acid and IL-15 induce inflammatory immunity to dietary antigens," *Nature* 471(7337), 220-224.
Eghtesad, S. et al. (2011) "Rapamycin ameliorates dystrophic phenotype in mdx mouse skeletal muscle," *Molecular Medicine* 17(9-10), 917-924.

Fernandez-Martin, A. et al. (2006) "Vasoactive intestinal peptide induces regulatory T cells during experimental autoimmune encephalomyelitis," *European Journal of Immunology* 36(2), 318-326.
First, M. R. (2002) "Immunosupressive agents and their actions," *Transplantation Proceedings* 34(5), 1369-1371.
Floess, S. et al. (2007) "Epigenetic Control of the foxp3 Locus in Regulatory T Cells," *PLoS Biology* 5(2), e38.
Fontenot, J. D. et al. (2003) "Foxp3 programs the development and function of CD4+CD25+ regulatory T cells," *Nature Immunology* 4(4), 330-336.
Fu, S. et al. (2004) "TGF-β Induces Foxp3+ T-Regulatory Cells from CD4+ CD25− Precursors," *American Journal of Transplantation* 4(10), 1614-1627.
Garlet, G. P. et al. (2005) "Actinobacillus actinomycetemcomitans-induced periodontal disease in mice: patterns of cytokine, chemokine, and chemokine receptor expression and leukocyte migration," *Microbes and Infection* 7(4), 738-747.
Garlet, G. P. et al. (2010) "Regulatory T cells attenuate experimental periodontitis progression in mice," *Journal of Clinical Periodontology* 37(7), 591-600.
Gonzalez-Rey, E. et al. (2007) "Vasoactive intestinal peptide and regulatory T-cell induction: a new mechanism and therapeutic potential for immune homeostasis," *Trends in Molecular Medicine* 13(6), 241-251.
Hariharan, S. et al. (2000) "Improved Graft Survival after Renal Transplantation in the United States, 1988 to 1996," *New England Journal of Medicine* 342(9), 605-612.
Haxhinasto, S. et al. (2008) "The AKT-mTOR axis regulates de novo differentiation of CD4+Foxp3+ cells," *Journal of Experimental Medicine* 205(3), 565-574.
Hippen, K. L. et al. (2011) "Generation and Large-Scale Expansion of Human Inducible Regulatory T Cells That Suppress Graft-Versus-Host Disease," *American Journal of Transplantation* 11(6), 1148-1157.
Hori, S. T. S. (2003) "Control of Regulatory T Cell Development by the Transcription Factor Foxp3," *Science* 299(5609), 1057.
Jhunjhunwala, S. et al. (2012) "Controlled release formulations of IL-2, TGF-β1 and rapamycin for the induction of regulatory T cells," *Journal of Controlled Release* 159(1), 78-84.
Jhunjhunwala, S. et al. (2009) "Delivery of rapamycin to dendritic cells using degradable microparticles," *Journal of Controlled Release* 133(3), 191-197.
Kawamoto, K. et al. (2010) "Transforming growth factor beta 1 (TGF-β1) and rapamycin synergize to effectively suppress human T cell responses via upregulation of FoxP3+ Tregs," *Transplant Immunology* 23(1-2), 28-33.
Khattri, R. et al. (2003) "An essential role for Scurfin in CD4+ CD25+ T regulatory cells," *Nature Immunology* 4(4), 337-342.
Kopf, H. et al. (2007) "Rapamycin inhibits differentiation of Th17 cells and promotes generation of FoxP3+ T regulatory cells," *International Immunopharmacology* 7(13), 1819-1824.
Kyekyoon, K. et al. (2006) "Microspheres for Drug Delivery," in *Biological and Biomedical Nanotechnology* (Lee, A. P., et al., Eds.), pp. 19-50, Springer, U.S.
Lee, I. et al. (2005) "Recruitment of Foxp3+ T regulatory cells mediating allograft tolerance depends on the CCR4 chemokine receptor," *Journal of Experimental Medicine* 201(7), 1037-1044.
Lee, W. L. et al. (2010) "Formation and degradation of biodegradable triple-layered microparticles," *Macromolecular Rapid Communications* 31(13), 1193-1200.
Lu, L. et al. (2010) "Characterization of protective human CD4CD25 FOXP3 regulatory T cells generated with IL-2, TGF-β and retinoic acid," *PLoS One* 5(12), e15150.
Makadia, H. K. et al. (2011) "Poly Lactic-co-Glycolic Acid (pLGA) as Biodegradable Controlled Drug Delivery Carrier," *Polymers* 3(3), 1377-1397.
Misaka, S. et al. (2010) "Inhalable powder formulation of a stabilized vasoactive intestinal peptide (VIP) derivative: Anti-inflammatory effect in experimental asthmatic rats," *Peptides* 31(1), 72-78.
Mucida, D. et al. (2007) "Reciprocal TH17 and regulatory T cell differentiation mediated by retinoic acid," *Science* 317(5835), 256-260.

(56) References Cited

OTHER PUBLICATIONS

Park, C. H. et al. (2007) "Three-dimensional micro-computed tomographic imaging of alveolar bone in experimental bone loss or repair," *Journal of Periodontology 78*(2), 273-281.

Pozo, D. et al. (2007) "Tuning immune tolerance with vasoactive intestinal peptide: A new therapeutic approach for immune disorders," *Peptides 28*(9), 1833-1846.

Putney, S. D. et al. (1998) "Improving protein therapeutics with sustained-release formulations," *Nature Biotechnology 16*(2), 153-157.

Raimondi, G. et al. (2010) "Mammalian Target of Rapamycin Inhibition and Alloantigen-Specific Regulatory T Cells Synergize to Promote Long-Term Graft Survival in Immunocompetent Recipients," *Journal of Immunology 184*(2), 624-636.

Riley, J. L. et al. (2009) "Human T Regulatory Cell Therapy: Take a Billion or So and Call Me in the Morning," *Immunity 30*(5), 656-665.

Robinson, D. S. et al. (2004) "Tregs and allergic disease," *Journal of Clinical Investigation 114*(10), 1389-1397.

Robinson et al. (2001) "Chapter 17. Generation of Murine Bone-Marrow-Derived Dendritic Cells," in *Dendritic Cell Protocols*, pp. 191-198.

Rothstein, S. N. et al. (2008) "A simple model framework for the prediction of controlled release from bulk eroding polymer matrices," *Journal of Materials Chemistry 18*(16), 1873-1880.

Rothstein, S. N. et al. (2009) "A unified mathematical model for the prediction of controlled release from surface and bulk eroding polymer matrices," *Biomaterials 30*(8), 1657-1664.

Safinia, N. et al. (2010) "Adoptive regulatory T cell therapy: challenges in clinical transplantation," *Current Opinion in Organ Transplantation 15*(4), 427-434.

Sakaguchi, S. et al. (1995) "Immunologic self-tolerance maintained by activated T cells expressing IL-2 receptor alpha-chains (CD25). Breakdown of a single mechanism of self-tolerance causes various autoimmune diseases," *Journal of Immunology 155*(3), 1151-1164.

Sakaguchi, S. et al. (2001) "Immunologic tolerance maintained by CD25+ CD4+ regulatory T cells: their common role in controlling autoimmunity, tumor immunity, and transplantation tolerance," *Immunological Reviews 182*(1), 18-32.

Sakaguchi, S. et al. (2008) "Regulatory T Cells and Immune Tolerance," *Cell 133*(5), 775-787.

Shevach, E. M. (2002) "CD4+CD25+ suppressor T cells: more questions than answers," *Nature Reviews Immunology 2*(6), 389-400.

Sigma-Aldrich. (2013) Biodegradable Polymers: RESOMER® Materials by Evonik Röhm GmbH.

Suntharalingam, G. et al. (2006) "Cytokine Storm in a Phase 1 Trial of the Anti-CD28 Monoclonal Antibody TGN1412," *New England Journal of Medicine 355*(10), 1018-1028.

Thomas, T. T. et al. (2004) "Microparticulate formulations for the controlled release of interleukin-2," *Journal of Pharmaceutical Sciences 93*(5), 1100-1109.

Thomson, A. W. et al. (2009) "Immunoregulatory functions of mTOR inhibition," *Nature Reviews Immunology 9*(5), 324-337.

Trzonkowski, P. et al. (2009) "First-in-man clinical results of the treatment of patients with graft versus host disease with human ex vivo expanded CD4+CD25+CD127-T regulatory cells," *Clinical Immunology 133*(1), 22-26.

Veldhoen, M. et al. (2006) "TGFβ in the Context of an Inflammatory Cytokine Milieu Supports De Novo Differentiation of IL-17-Producing T Cells," *Immunity 24*(2), 179-189.

Von Boehmer, H. (2003) "Dynamics of Suppressor T Cells: In Vivo Veritas," *Journal of Experimental Medicine 198*(6), 845-849.

Wang, H. et al. (2008) "TGF-beta-dependent suppressive function of Tregs requires wild-type levels of CD18 in a mouse model of psoriasis," *Journal of Clinical Investigation 118*(7), 2629-2639.

Webster, K. E. et al. (2009) "In vivo expansion of T reg cells with IL-2-mAb complexes: induction of resistance to EAE and long-term acceptance of islet allografts without immunosuppression," *Journal of Experimental Medicine 206*(4), 751-760.

Wernig, K. et al. (2008) "Depot formulation of vasoactive intestinal peptide by protamine-based biodegradable nanoparticles," *Journal of Controlled Release 130*(2), 192-198.

Wieckiewicz, J. et al. (2010) "T regulatory cells and the control of alloimmunity: from characterisation to clinical application," *Current Opinion in Immunology 22*(5), 662-668.

Yamaguchi, T. et al. (2007) "Control of Immune Responses by Antigen-Specific Regulatory T Cells Expressing the Folate Receptor," *Immunity 27*(1), 145-159.

\* cited by examiner

A

B

CONTROLLED RELEASE FORMULATIONS FOR THE INDUCTION AND PROLIFERATION OF BLOOD CELLS

STATEMENT OF GOVERNMENT INTEREST

This invention was made with government support under grant numbers RR024154 and AI067541 awarded by the National Institutes of Health. The government has certain rights in the invention.

FIELD OF THE INVENTION

The present invention is related to the treatment of immunological disorders, immunological diseases and/or transplantation rejection reactions. For example, certain embodiments of the invention result in the specific targeting of blood cells including but not limited to naive blood cells and/or white blood cells (e.g., T cells and/or B cells) to affected tissues. In particular, the tissue targeting of the regulatory T cells may be accomplished by custom designed microparticles that provide a pre-determined controlled release of T cell inducing factors or combination of T cell inducing factors. Consequently, a plurality of microparticles may release inducing factors that differ both temporally and spatially resulting in a specific migration behavior or activation of the target T cell population.

BACKGROUND

The science of transplantation, now half of a century old, has dramatically increased and improved the life of many individuals, including many children, with end stage diseases. Recent advancements in immunosuppressive agents have substantially decreased rejection of allografts over the past decade and a half in the United States. Hariharan et al., *N Engl J Med* 342, 605-612 (2000); and First, M. R., *Transplant Proc* 34:1369-1371 (2002). However, to avoid both episodes of acute rejection and the initiation of chronic rejection following transplantation, immunosuppressive drugs must be administered over the entire life of the organ recipient.

Consequences of this long-term administration are profound, including undesirable side effects, increasing the risk of infection, autoimmunity, heart disease, diabetes, and cancer. The chronic administration of these immunosuppressive drugs (especially when give systemically) lead to toxicity and significant side effects, thereby leaving the patient vulnerable to a variety of diseases and systemic organ failure. The most desirable alternative to this extended state of vulnerability would be to render the patient's immune system to effectively suppress immune activation without systemic immunosuppression. In this case, no further immunosuppressant drug treatment would be necessary. Furthermore, the recipient's immune system would otherwise function normally, being capable of combating pathogens and malignant tumor cells. What is needed in the art are compositions and methods to specifically target induced regulatory T cells to specific tissues affected by immunological disorders.

SUMMARY

The present invention is related to the treatment of immunological disorders, immunological diseases and/or transplantation rejection reactions. For example, certain embodiments of the invention result in the specific targeting of blood cells including but not limited to naive blood cells and/or white blood cells (e.g., T cells and/or B cells) to affected tissues. In particular, the tissue targeting of the regulatory T cells may be accomplished by custom designed microparticles that provide a pre-determined controlled release of T cell inducing factors or combination of T cell inducing factors. Consequently, a plurality of microparticles may release inducing factors that differ both temporally and spatially resulting in a specific migration behavior or activation of the target T cell population.

In one embodiment, the present invention contemplates a method comprising: a) providing; i) a patient comprising a target tissue and a blood cell population, wherein the target tissue exhibits at least one symptom of a disease; and ii) a plurality of microparticle populations wherein each of the microparticle populations comprise a different compound, and wherein each of the microparticle populations releases the different compound with a different release profile; b) administering the microparticle to the patient under conditions such that the blood cell population is induced; and c) migrating the induced blood cell population to the target tissue. In one embodiment, the target tissue is a lymph node tissue. In one embodiment, the target tissue is an intestinal (e.g., gut) tissue. In one embodiment, the target tissue exhibits at least one symptom of a disease. In one embodiment, the method further comprises reducing the target tissue at least one symptom of a disease with the migrated induced blood cell population. In one embodiment, the disease comprises an immunological disease. In one embodiment, the different compound is a regulatory T cell inducing factor. In one embodiment, the regulatory T cell inducing factor includes but is not limited to IL-2, vasoactive intestinal peptide, transforming growth factor beta (TGF-β), rapamycin and/or retinoic acid. In one embodiment, the blood cell is a white blood cell. In one embodiment, the white blood cell is a T cell. In one embodiment, the T cell is a regulatory T cell. In one embodiment, the white blood cell is a B cell. In one embodiment, the blood cell is a naive blood cell. In one embodiment, each of the plurality of microparticle populations comprises a different polymer composition predicted by a mathematical algorithm. In one embodiment, the different polymer composition determines the different release profile. In one embodiment, the different polymer composition comprises a 4.2 kDa polymer, a 12.6 kDa polymer and a 55 kDa polymer. In one embodiment, the different polymer composition comprises a 4.2 kDa polymer, a 12.6 kDa polymer and a 100 kDa polymer.

In one embodiment, the present invention contemplates a microparticle comprising a 4.2 kDa polymer, a 12.6 kDa polymer and a 100 kDa polymer. In one embodiment, the microparticle further comprises a compound. In one embodiment, the compound is vasoactive intestinal peptide. In one embodiment, the microparticle is comprised of 10.6% of the 4.2 kDa polymer. In one embodiment, the microparticle is comprises of 31.9% of the 12.6 kDa polymer. In one embodiment, the microparticle is comprised of 57.5% of the 100 kDa polymer. In one embodiment, the microparticle further comprises polyethylene glycol.

In one embodiment, the present invention contemplates a microparticle comprising a 4.2 kDa polymer, a 12.6 kDa polymer and a 55 kDa polymer. In one embodiment, the microparticle further comprises a compound. In one embodiment, the compound is vasoactive intestinal peptide. In one embodiment, the microparticle is comprised of 33.3% of the 4.2 kDa polymer. In one embodiment, the microparticle is comprises of 33.3% of the 12.6 kDa polymer. In one embodiment, the microparticle is comprised of 33.3% of the 55 kDa polymer. In one embodiment, the 12.6 kDa polymer is an RG502H polymer. In one embodiment, the 55 kDA polymer is an RG505 polymer. In one embodiment, the microparticle further comprises polyethylene glycol.

In one embodiment, the present invention contemplates a method comprising: a) providing; i) a patient comprising a target tissue and a blood cell population, wherein the target tissue exhibits at least one symptom of a disease; and ii) a plurality of microparticle populations wherein each of the microparticle populations comprise a different compound, and wherein each of the microparticle populations releases the different compound with a different release profile; b) administering the microparticle to the patient under conditions such that the blood cell population is induced; and c) migrating the induced blood cell population to the target tissue. In one embodiment, the target tissue is a pancreatic tissue. In one embodiment, the induced blood cell population drains into a pancreatic lymph node. In one embodiment, the disease comprises Type I diabetes. In one embodiment, the target tissue exhibits at least one symptom of a disease. In one embodiment, the target tissue is epithelial tissue. In one embodiment, the induced blood cell population drains into a popliteal lymph node. In one embodiment, the induced blood cell population drains into an inguinal lymph node. In one embodiment, the disease comprises contact dermatitis. In one embodiment, the method further comprises reducing the target tissue at least one symptom of a disease with the migrated induced blood cell population. In one embodiment, the disease comprises an immunological disease. In one embodiment, the different compound is a regulatory T cell inducing factor. In one embodiment, the regulatory T cell inducing factor includes, but is not limited to, IL-2, vasoactive intestinal peptide, transforming growth factor beta (TGF-β), rapamycin, retinoic acid, and/or IL-10. In one embodiment, the blood cell is a white blood cell. In one embodiment, the white blood cell is a T cell. In one embodiment, the T cell is a regulatory T cell. In one embodiment, the white blood cell is a B cell. In one embodiment, the blood cell is a naive blood cell. In one embodiment, each of the plurality of microparticle populations comprises a different polymer composition predicted by a mathematical algorithm. In one embodiment, the different polymer composition determines the different release profile. In one embodiment, the different polymer composition comprises approximately 5 kilodaltons polyethylene glycol (PEG) at a concentration of approximately 4-6 wt % and a poly(lactide-co-glycolide) polymer (PLGA). In one embodiment, the PLGA is approximately between 7-17 kilodaltons (e.g., RG502H). In one embodiment, the PLGA is approximately between 24-38 kilodaltons (e.g., RG503H). In one embodiment, the PLGA is approximately between 38-54 kilodaltons (e.g., RG504H). In one embodiment, the PEG and PLGA is a diblock copolymer. In one embodiment, the PEG and PLGA is a PLGA+PLGA-PEG diblock copolymer. In one embodiment, the microparticle ranges in diameter between approximately 200-1000 nanometers.

In one embodiment, the present invention contemplates a microparticle comprising approximately 5 kilodaltons polyethylene glycol (PEG) at a concentration of approximately 4-6 wt % and a poly(lactide-co-glycolide) polymer (PLGA). In one embodiment, the PLGA is approximately between 7-17 kilodaltons (e.g., RG502H). In one embodiment, the PLGA is approximately between 24-38 kilodaltons (e.g., RG503H). In one embodiment, the PLGA is approximately between 38-54 kilodaltons (e.g., RG504H). In one embodiment, the PEG and PLGA is a diblock copolymer. In one embodiment, the PEG and PLGA is a PLGA+PLGA-PEG diblock copolymer. In one embodiment, the microparticle ranges in diameter between approximately 200-1000 nanometers.

In one embodiment, the present invention contemplates a kit comprising: a) a first container comprising a "FactorMP" composition; b) a second container comprising a pharmaceutically acceptable vehicle for administration of the composition; and c) instructions for administering the composition to a patient comprising a target tissue exhibiting at least one symptom of a disease. In one embodiment, the "FactorMP" composition comprises an IL-2MP composition. In one embodiment, the "FactorMP" composition comprises a TGF-β composition. In one embodiment, the "FactorMP" composition comprises a rapamycinMP composition. In one embodiment, the "FactorMP" composition comprises a VIPMP composition. In one embodiment, the "FactorMP" composition comprises an IL-2MP composition.

Definitions

The term "target tissue" as used herein, refers to any bodily tissue that may be affected by a medical condition and/or disorder (e.g., an immunological disease) to which a populations of regulatory T cells may be directed to by induction with a combination of T cell inducing factors released from microparticles having pre-determined release profiles.

The term "blood cell" as used herein, refers to any biological cell, either nucleated or enucleated, found circulating in the blood stream.

The term "white blood cell as used herein, refers to any blood cell that is colorless, lacks hemoglobin, contains a nucleus, and may include but is not limited to lymphocytes, monocytes, neutrophils, eosinophils, and basophils—called also leukocyte, white blood corpuscle, white cell, and/or white corpuscle.

The term "T cell" as used herein, refers to any of several lymphocytes (e.g., helper T cell or regulatory T cell) that differentiate in the thymus, possess highly specific cell-surface antigen receptors, and include some that control the initiation or suppression of cell-mediated and humoral immunity (as by the regulation of T and B cell maturation and proliferation) and others that lyse antigen-bearing cells—also referred to as a T lymphocyte The term "B cell" as used herein, refers to any of the several lymphocytes that have antigen-binding antibody molecules on the surface, that comprise the antibody-secreting plasma cells when mature, and that in mammals differentiate in the bone marrow—also referred to as a B lymphocyte.

The term "microparticle population" as used herein, refers to a collection of microparticles having similar properties and composition.

The term "polymer" as used herein, refers to any unit-based chain of molecules. For example, such molecules may include but are not limited to gelatin, collagen, cellulose esters, dextran sulfate, pentosan polysulfate, chitin, saccharides, albumin, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

The term, "microparticle" as used herein, refers to any microscopic carrier to which a compound or drug may be attached. Preferably, microparticles contemplated by this invention are capable of formulations having controlled release properties.

The term "PLGA" as used herein, refers to mixtures of polymers or copolymers of lactic acid and glycolic acid. As used herein, lactide polymers are chemically equivalent to lactic acid polymer and glycolide polymers are chemically equivalent to glycolic acid polymers. In one embodiment, PLGA contemplates an alternating mixture of lactide and glycolide polymers, and is referred to as a poly(lactide-co-glycolide) polymer.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "transplant rejection reaction" or "graft versus host disease" as used herein, refers to any activation of the immune system subsequent to the implantation of an exogenous tissue and/or organ into a patient that may result in damage and/or destruction of the transplanted tissue. Generally, transplant rejections are believed to be an adaptive immune response via cellular immunity (i.e., for example, mediated by killer T cells inducing apoptosis of target cells) as well as humoral immunity (mediated by activated B cells secreting antibody molecules), though the action is joined by components of innate immune response (phagocytes and soluble immune proteins).

The term "disease", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "migration" or "migrate" or "migrating" as used herein, refers to any movement of a cell (e.g., a T cell) in the direction of a compromised target tissue. Such migration may be accompanied by the stimulation of chemotactic factors (i.e., for example, lysophosphatidic acid) released by white blood cells.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term, "purified" or "isolated", as used herein, may refer to a peptide composition that has been subjected to treatment (i.e., for example, fractionation) to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single protein species (i.e., for example, based upon SDS-PAGE or HPLC analysis). A purified composition is not intended to mean that some trace impurities may remain.

As used herein, the term "substantially purified" refers to molecules, either nucleic or amino acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The term "immunologically active" defines the capability of a natural, recombinant or synthetic peptide, or any oligopeptide thereof, to induce a specific immune response in appropriate animals or cells and/or to bind with specific antibodies.

BRIEF DESCRIPTION OF THE FIGURES

FIG. 1A: Flow cytometry density plots indicating % of CD4+ cells that express FoxP3 (representative of 6 independent experiments). Plots were generated after gating on CD4+ cells.

FIG. 1B: Quantitative analysis of the % of CD4+ that express FoxP3. * indicates $p<0.05$, and ** indicates $p<0.01$ when the specified group was compared to the TGFβ-iTreg group using the paired Student's 't' test (based on $n \geq 6$).

FIG. 1C: Representative histograms (at least 2 independent experiments) for canonical markers expressed on Treg. Plots were generated after gating on CD4+ FoxP3+ cells. Numbers on plots represent median fluorescent intensities. Filled gray histograms represent isotypes.

FIG. 4A: Quantitative analysis of the fold change in % FoxP3+ iTreg after in vitro re-stimulation in the absence of Treg-inducing factors.

FIG. 4B: Quantitative analysis of the fold change in % FoxP3+ iTreg after in vitro re-stimulation in the presence of Treg-inducing factors.

FIG. 5A: Histograms depicting expression patterns of different migratory receptors; plotted after gating on CD4+ FoxP3+ cells. Numbers on plots represent MFI values.

FIG. 5B: Quantitative analysis of CCR7 expression on iTreg generated under different conditions (MFI values were normalized to TGFβ-iTreg cells). * indicates $p<0.05$ (paired Student's 't' test) when comparing specified group to RA-iTreg group; n=5.

FIG. 5C: iTreg generated from CD45.1+ were injected into CD45.2+ mice and after 3 days, C-Ln (cervical lymph nodes) and M-Ln (mesenteric lymph nodes) harvested to analyze the percentage of CD45.1+ cells. * indicates $p<0.05$ when comparing specified group to either the TGFβ-iTreg or RA-iTreg groups.

FIG. 8A: Representative images acquired using the IVIS 200, showing iTreg cell population localization over 10 days. Red ellipses indicate the cervical lymph node (small ellipse) and gut area (large ellipse).

Figure 8:
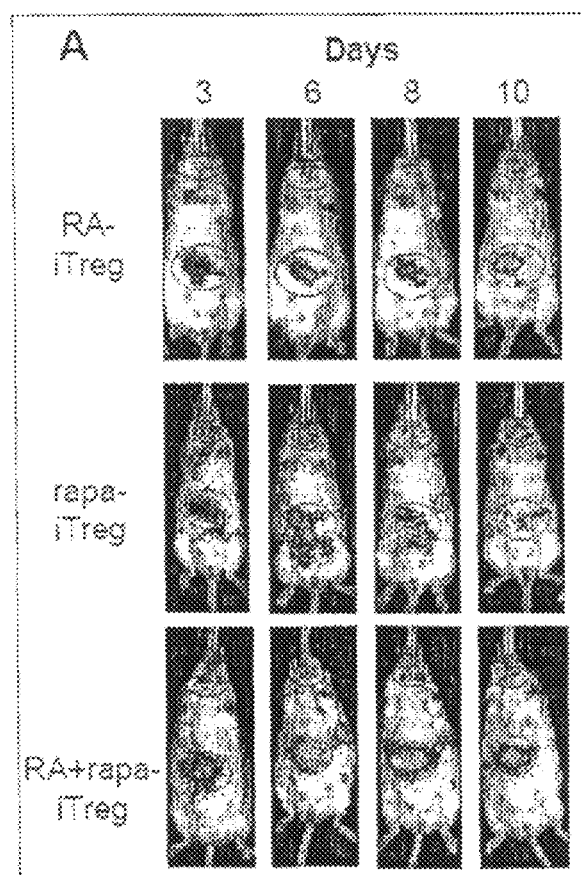
FIG. 8 presents exemplary data showing in vivo imaging of iTreg cell population localization following injection.
Figure 8:
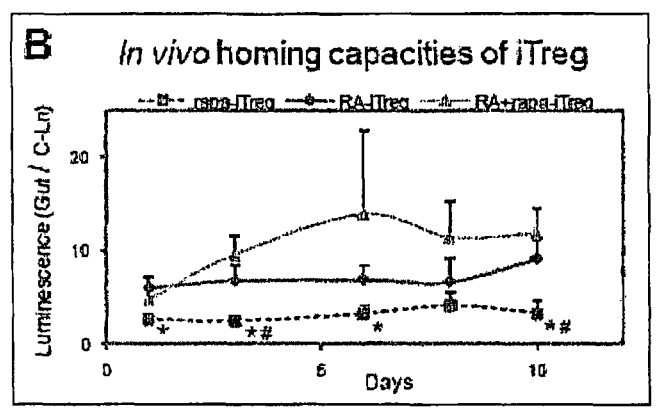

FIG. 8B: A ratio of the average luminescence measurements obtained from the red ellipses depicted as a function of time. * indicates p≤0.05 when comparing rapa-iTreg with RA-iTreg and # indicates p≤0.05 when comparing rapa-iTreg with RA+rapa-iTreg. n≥3 mice for all groups. C-Ln indicates the cervical lymph node area.

Figure 9:
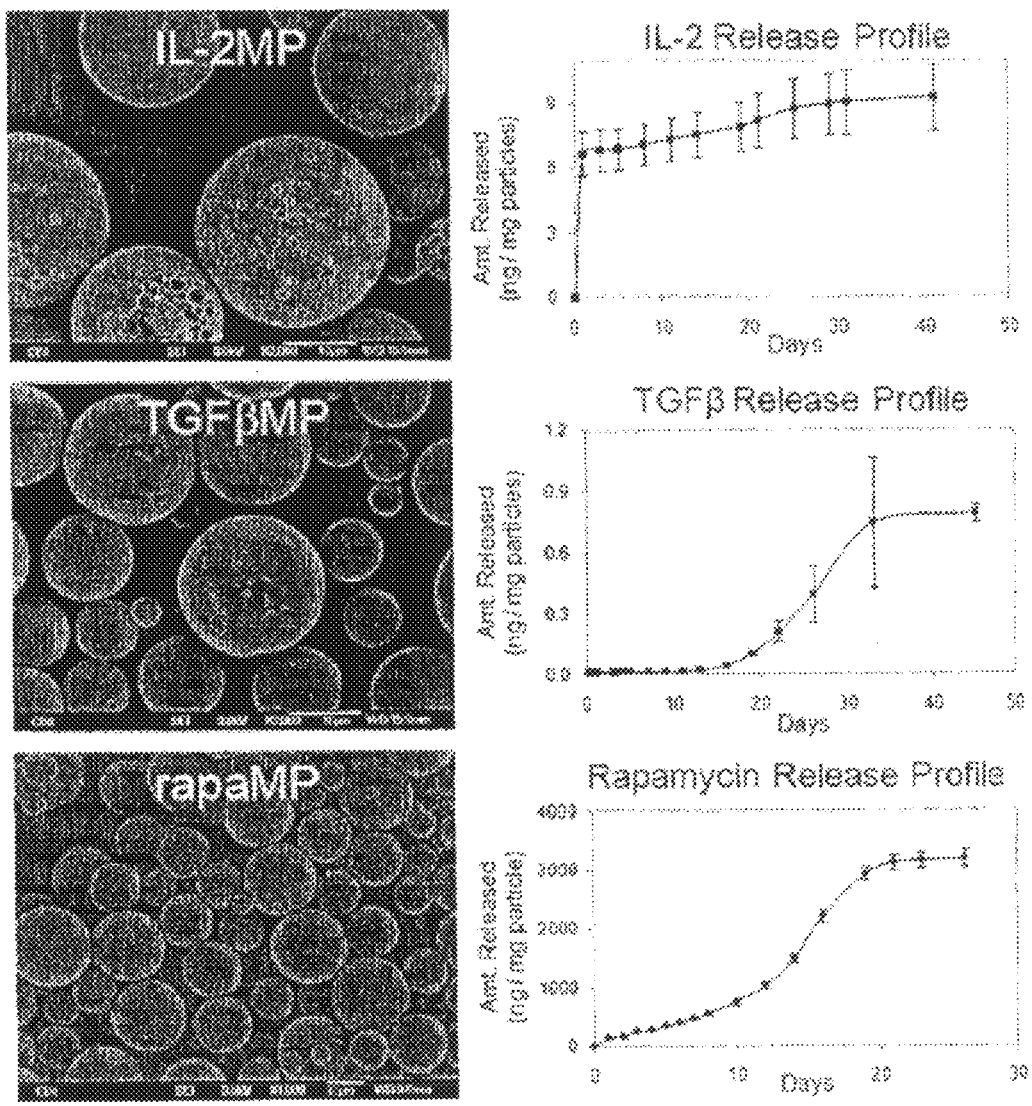

FIG. 9 presents exemplary data showing micropartcles comprising mathematically predicted release characteristics of T cell inducing factors. Scanning electron micrographs (left panel) and in vitro release profiles (right panel) of IL-2, TGFβ (in cell culture media) and rapa (in saline containing 0.2% Tween-80). Error bars on release profiles represent standard deviation based on n=6 measurements for IL-2MP and TGFβMP, and n=3 measurements for rapaMP.

Figure 10:
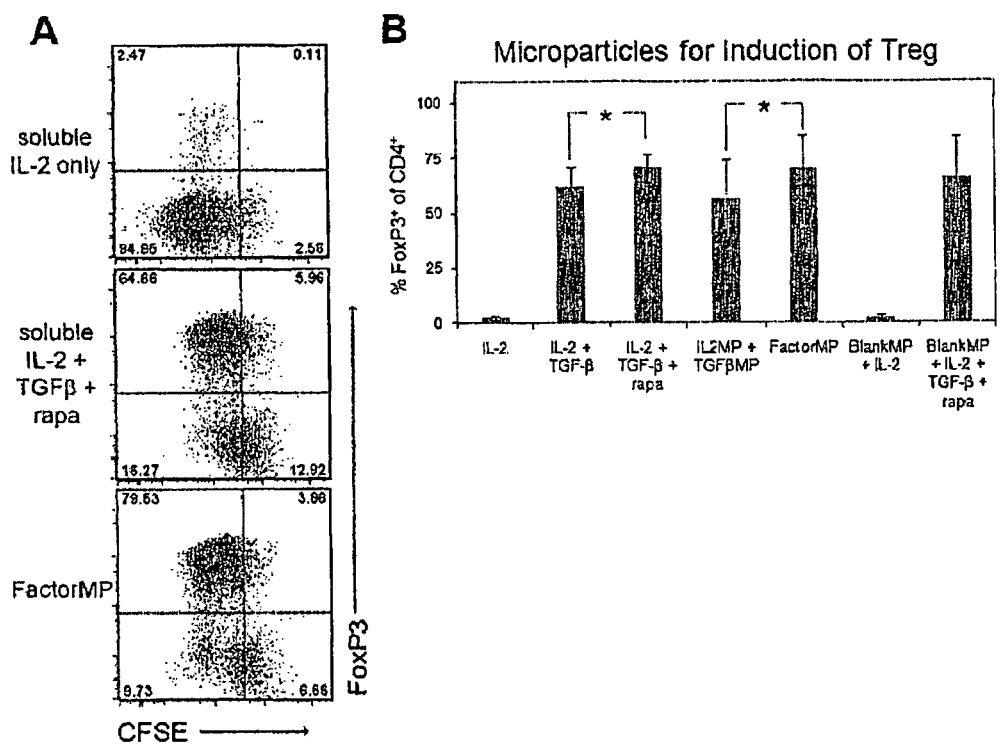

FIG. 10 presents exemplary data showing that "Factor" MPs induce mouse Treg cell populations.

FIG. 10A: Representative flow cytometry dot plots (gated on CD4-expressing cells) of naïve T cells stimulated in the presence of soluble factors or FactorMP. The X axis on these plots represents CFSE, which is a cell proliferation marker and the Y axis represents intracellular FoxP3, which is a definitive marker for mouse Treg cells.

FIG. 10B: Quantitative analysis of the percentage of CD4+ T cells that express FoxP3 after culture for 4 days under different conditions; * indicates p<0.05 based on n≥3 independent experiments.

Figure 11:
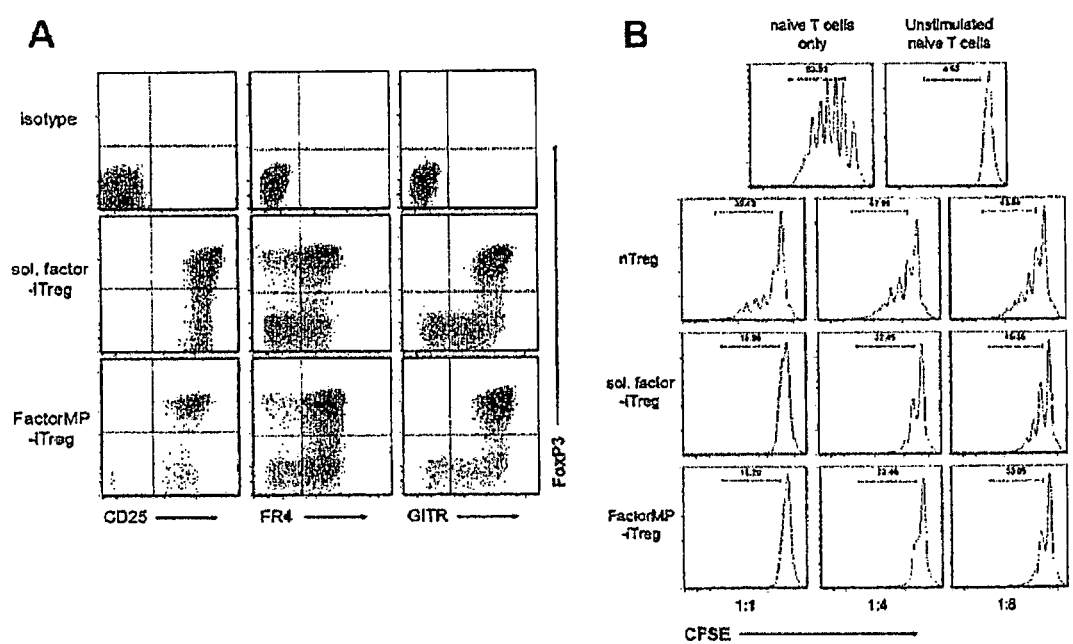

FIG. 11 presents exemplary data showing that "Factor" MP-iTreg cell populations express several canonical Treg surface markers and suppress effector T cells.

FIG. 11A: Representative flow cytometry dot plots (gated on CD4-expressing cells) showing the expression of surface markers and intracellular FoxP3 on naïve T cells stimulated in the presence of soluble factors or "Factor" MPs.

Figure 12:
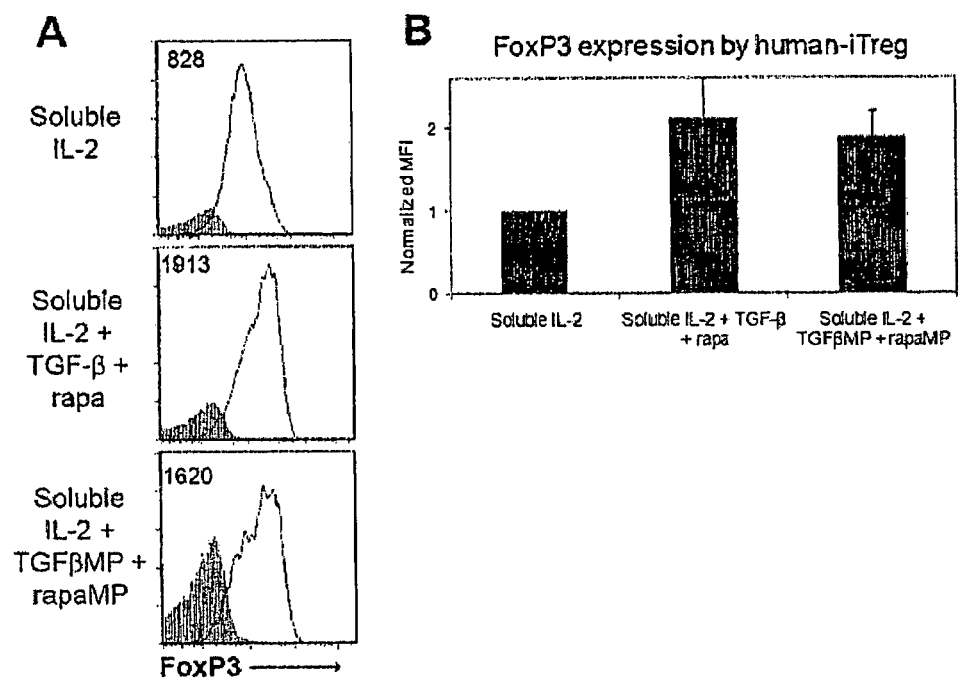

FIG. 11B: Representative plots of CFSE dilution showing that the "Factor" MP-iTreg can suppress naïve T cell proliferation. Gates on individual plots indicate the percentage of proliferating cells. Ratios indicate the number of Treg cells in culture to the number of naïve T cells. Data are representative of at least 2 independent experiments FIG. 12 presents exemplary data showing that "Factor" MP populations generate human-iTreg equivalent to those induced by soluble T cell inducing factors.

FIG. 12A: Representative plots displaying FoxP3 expression profile on human T cells cultured under different conditions. Numbers in plots represent the median fluorescence intensities (MFI). Grey plots indicate the FoxP3 expression in naïve unstimulated T cells.

FIG. 12B: Quantitative analysis of normalized FoxP3 MFI as determined from 2 independent experiments (n≥3). MFI was normalized by determining the ratio of experimental MFI and control (soluble IL-2 treated cells) MFI.

Figure 13:
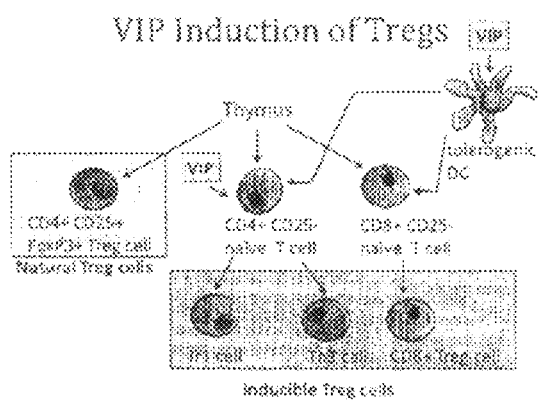
Figure 14:
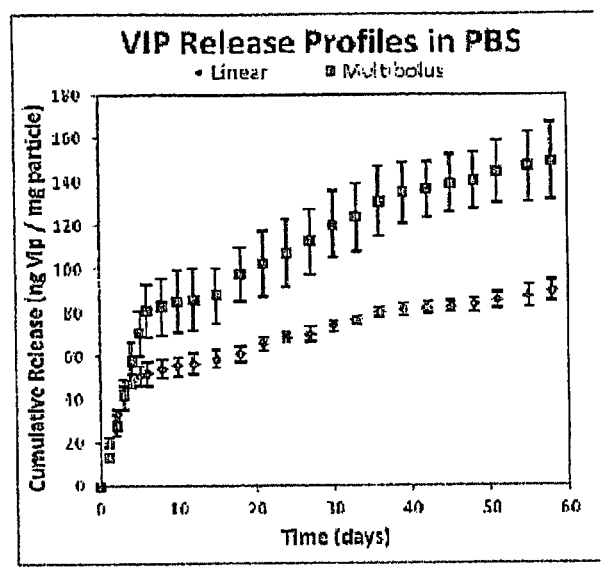
Figure 14:
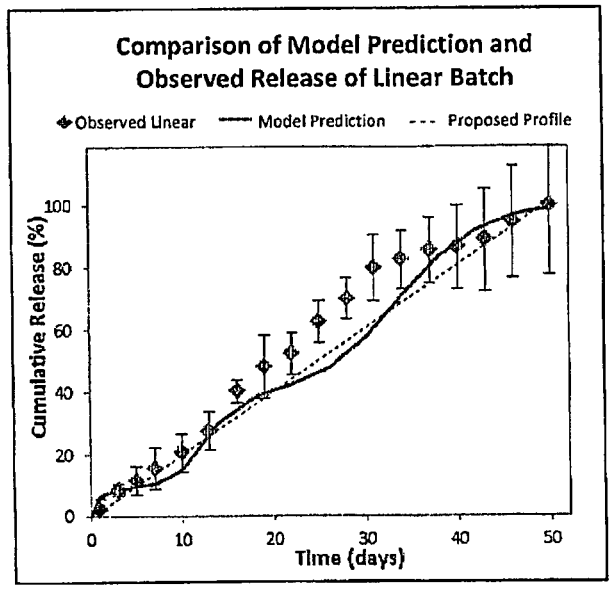

FIG. 13 presents a representative schematic of proposed mechanism for vasoactive intestinal peptide (VIP) induction of regulatory T cells. One mechanism may be a direct activation of CD4+CD25− naïve T cells to inducible Tregs. Another mechanisms may involve activation of tolerogenic dendritic cells which then promote inducible Treg generation through activation of CD8+CD25− naïve T cells FIG. 14 presents exemplary data showing VIP release from VIPMPs having predicted release profiles.

FIG. 14A: Release assays of predicted linear release VIPMPs and predicted multi-bolus release VIPMPs. Standard deviations are represented by bars at each data point.

FIG. 14B. Comparison of the algorithmic model release prediction (red) and observed (blue) release of VIP from the predicted linear release VIPMPs ignoring the anaomalous initial release burst. The desired profile input to the model is represented by the dashed line.

Figure 15:
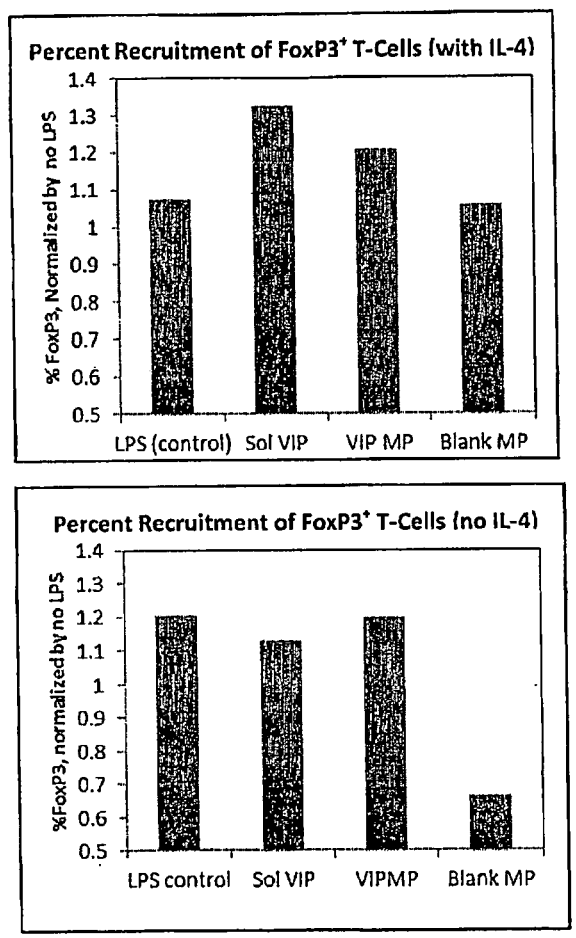

FIG. 15 presents exemplary data showing the percent of FoxP3+ CD4+ t-cells which were recruited through the transwells by DCs, following treatment with LPS and addition of soluble VIP ($2.5 \times 10^{-8}$ M), blank microparticles releasates, or VIP microparticle releasates (estimated to be at $2.5 \times 10^{-8}$ M from previous release profiles). Percents were normalized by the group which did not receive LPS. Upper Graph: DC precursors treated with IL-4 and GM-CSF. Lower Graph: DC precursors cultured with 5× GM-CSF.

Figure 16:
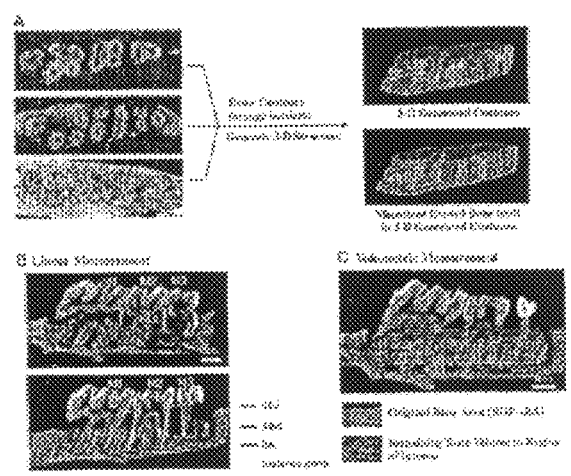

FIG. 16 presents exemplary data showing linear and volumetric measurements of alveolar bone loss using micro-CT imaging following "Factor" MP administration.

DETAILED DESCRIPTION

The present invention is related to the treatment of immunological disorders, immunological diseases and/or transplantation rejection reactions. For example, certain embodiments of the invention result in the specific targeting of blood cells including but not limited to naive blood cells and/or white blood cells (e.g., T cells and/or B cells) to affected tissues. In particular, the tissue targeting of the regulatory T cells may be accomplished by custom designed microparticles that provide a pre-determined controlled release of T cell inducing factors or combination of T cell inducing factors. Consequently, a plurality of microparticles may release inducing factors that differ both temporally and spatially resulting in a specific migration behavior or activation of the target T cell population.

Current techniques for regulatory T cell induction can only be used in vitro as they rely on the use of soluble mediators. In some embodiments, the present invention contemplates compositions and methods to deliver T cell induction soluble factors in vivo in a sustained, predictable and controlled manner.

I. Regulatory T Cells

A. Immunological Role And Function Over the past two decades, regulatory T cells (Treg) have been identified as one of the central components of the mammalian immune system. Sakaguchi et al., "Immunologic tolerance maintained by CD25+ CD4+ regulatory T cells: their common role in controlling autoimmunity, tumor immunity, and transplantation tolerance" *Immunol Rev.* (2001) 182:18-32; Sakaguchi et al., "Regulatory T cells and immune tolerance" *Cell* (2008) 133:775-787; Campbell et al., "Phenotypical and functional specialization of FOXP3+ regulatory T cells" *Nat Rev Immunol* (2011) 11:119-130; and Bour-Jordan et al., "Regulating the regulators: costimulatory signals control the homeostasis and function of regulatory T cells" (2009) 229:41-66. The most commonly described, widely studied, and possibly most abundant regulatory T cells in the body are those that express CD4, CD25, and/or FoxP3. These CD4+ CD25+ FoxP3+ cells (Treg) play important roles in suppressing the activity of self-reactive immune cells and in re-establishing homeostasis following infection. Sakaguchi et al., "Immunologic self-tolerance maintained by activated T cells expressing IL-2 receptor alpha-chains (CD25). Breakdown of a single mechanism of self-tolerance causes various autoimmune diseases" *J Immunol.* (1995) 155:1151-1164; Hori et al., "Control of regulatory T cell development by the transcription factor Foxp3" *Science* (2003) 299:1057-1061; Fontenot et al., "Foxp3 programs the development and function of CD4+CD25+ regulatory T cells" *Nat Immunol.*

(2003) 4:330-336; and Khattri et al., "An essential role for Scurfin in CD4+CD25+ T regulatory cells" *Nat Immunol.* (2003) 4:337-342.

B. Clinical Applications

Treg proliferation has been reported to suppress diverse inflammatory diseases such as: i) autoimmunity (de Kleer et al., "CD4+CD25bright regulatory T cells actively regulate inflammation in the joints of patients with the remitting form of juvenile idiopathic arthritis" *J Immunol.* (2004) 172: 6435-6443: ii) transplant rejection (Raimondi et al., "Mammalian target of rapamycin inhibition and alloantigen-specific regulatory T cells synergize to promote long-term graft survival in immunocompetent recipients" *J Immunol* (2010) 184:624-636; and Lee et al., "Recruitment of Foxp3+ T regulatory cells mediating allograft tolerance depends on the CCR4 chemokine receptor" *J Exp Med* (2005) 201:1037-1044; iii) dermatitis (Robinson et al., "Tregs and allergic disease" *J Clin Invest.* (2004) 114:1389-1397; iv) psoriasis (Wang et al., "TGF-beta-dependent suppressive function of Tregs requires wild-type levels of CD 18 in a mouse model of psoriasis" *J Clin Invest.* (2008) 118:2629-2639; Bovenschen et al., "Foxp3+ Regulatory T Cells of Psoriasis Patients Easily Differentiate into IL-17A-Producing Cells and Are Found in Lesional Skin" *J Invest Dermatol.* (2011) 131:1853-1860; and v) periodontitis Garlet et al., "Actinobacillus actinomycetemcomitans-induced periodontal disease in mice: patterns of cytokine, chemokine, and chemokine receptor expression and leukocyte migration" *Microbes Infect* (2005) 7:738-747; Garlet et al., "Regulatory T cells attenuate experimental periodontitis progression in mice" *J Clin Periodontol.* (2010) 37:591-600.

Proliferation of Treg cell populations at local tissue sites has been reported by various methods such as: i) ex vivo expansion of Treg cells followed by a local administration or systemic re-infusion; and ii) in vivo manipulation of immune cells that increases the Treg/Teff ratio. Riley et al., "Human T regulatory cell therapy: take a billion or so and call me in the morning" *Immunity* (2009) 30:656-665; Safinia et al., "Adoptive regulatory T cell therapy: challenges in clinical transplantation" *Curr Opin Organ Transplant* (2010) 15:427-434; and Wieckiewicz et al., "T regulatory cells and the control of alloimmunity: from characterisation to clinical application" *Curr Opin Immunol.* (2010) 22:662-668. Selective enhancement of Treg cell populations in vivo has been reported using biologic therapies. For example, i) anti-IL-2 monoclonal antibody (Webster et al., "In vivo expansion of T reg cells with IL-2-mAb complexes: induction of resistance to EAE and long-term acceptance of islet allografts without immunosuppression" *J Exp Med.* (2009) 206:751-760; ii) superagonistic anti-CD28 monoclonal antibody (Beyersdorf et al., "Selective targeting of regulatory T cells with CD28 superagonists allows effective therapy of experimental autoimmune encephalomyelitis" *J Exp Med.* (2005) 202:445-455; and iii) agonistic anti-CD4 monoclonal antibody (_____ "Deal watch: Boosting TRegs to target autoimmune disease" *Nat. Rev. Drug Discovery* (2011) 10:566. These approaches have specific disadvantages including but not limited to a limited understanding of the underlying mechanism of action and human safety for clinical administration remains a question. In fact, phase I clinical trials of the superagonistic anti-CD28 monoclonal antibody (TGN1412) resulted in severe negative reactions (cytokine 'storm') in all 6 human subjects who received the monoclonal antibody. Suntharalingam et al., "Cytokine storm in a phase 1 trial of the anti-CD28 monoclonal antibody TGN1412" *N Engl J Med.* (2006) 355:1018-1028. Establishment of a local immunosuppressive environment that selectively favors Treg expansion has also been shown to increase Treg cell population numbers. An environment rich in IL-2, transforming growth factor-β1 (TGF-β) and rapamycin (an inhibitor of the serine-threonine kinase mammalian target of rapamycin; mTOR) has been shown to favor Treg development, even under inflammatory conditions. Haxhinasto et al., "The AKT-mTOR axis regulates de novo differentiation of CD4+Foxp3+ cells" *J Exp Med.* (2008) 205:565-574; Kopf et al., "Rapamycin inhibits differentiation of Th17 cells and promotes generation of FoxP3+ T regulatory cells" *Int Immunopharmacol.* (2007) 7:1819-1824; and Cobbold et al., "Infectious tolerance via the consumption of essential amino acids and mTOR signaling" *Proc Natl Acad Sci USA* (2009) 106:12055-12060. However, formulations providing a predictable continuous release of these factors in vivo, has proven difficult. This problem is solved by the compositions and methods described herein showing predictable and differential controlled release of Treg cell inducing compounds from the same formulation. These compositions are expected to have a better therapeutic efficacy and safety than current antibody Treg induction models, thereby having a superior clinical application to treat medical disorders and disease.

Therapies that enhance Treg numbers and function may have the potential to suppress transplant rejection and autoimmunity. Clinical trials are currently testing cellular therapies involving Treg cells as potential therapeutics for treating graft versus host disease. Hippen et al., "Generation and large-scale expansion of human inducible regulatory T cells that suppress graft-versus-host disease" *Am J Transplant.* (2011) 11:1148-1157; and Brunstein et al., "Infusion of ex vivo expanded T regulatory cells in adults transplanted with umbilical cord blood: safety profile and detection kinetics" *Blood* (2011) 117:1061-1070. However, Treg-based cellular therapies face many challenges, which include, but are not limited to: i) difficulties in isolating pure and homogenous populations and large quantities of Treg from the blood; ii) inconsistent maintenance of the Treg phenotype and suppressive function post-proliferation; and iii) the need for GMP facilities. Riley et al., "Human T regulatory cell therapy: take a billion or so and call me in the morning" *Immunity* (2009) 30:656-665; Safinia et al., "Adoptive regulatory T cell therapy: challenges in clinical transplantation" *Curr Opin Organ Transplant.* (2010) 15:427-434; and Wieckiewicz et al., "T regulatory cells and the control of alloimmunity: from characterisation to clinical application" *Curr Opin Immunol.* (2010) 22:662-668. Hence, acellular therapies that can increase numbers and/or the suppressive potency of Treg without the need for ex vivo culture represent an answer to a long unsolved problem in the art.

II. Induction of Regulatory T Cell Phenotypes

Treg can be induced under a variety of in vitro and in vivo conditions. Treg induced under different conditions have distinct characteristics that distinguish them from each other and from naturally-occurring Treg. Identification of these distinctive characteristics provides insight into their potential use in treating inflammatory disorders (such as autoimmunity and allergy) and transplant rejection, or in preventing tumor growth and metastasis. For example, it has been demonstrated that RA can help to convert naïve T cells to Treg. These RA-iTreg are stable under inflammatory conditions and have the potential to prevent inflammation in the gut due primarily to their ability to specifically migrate to the gut. However, gut homing specificity could potentially be a hindrance to using these cells to treat autoimmunity or transplant rejection at other peripheral sites.

Regulatory T cells (Treg) may be involved in maintaining immune homeostasis. Consequently, it is believed that Treg therapy might be useful to treat medical conditions including but not limited to a variety of immune mediated disorders. Current Treg-based clinical therapies have disadvantages including but not limited to obtaining insufficient numbers of cells from peripheral blood for expansion and re-infusion. Alternative methods to induce the formation of Treg cells from non-Treg cells have been reported, usually by contacting the non-Treg cells with a soluble cytokine (e.g., TGF-β). However, this approach has disadvantages including but not limited to the fact that these methods do not induce stable Treg cells in sufficient number to be useful. Although it is not necessary to understand the mechanism of an invention, it is believed that all-trans retinoic acid (RA) and/or rapamycin (rapa) may aid in achieving a stable induced Treg (iTreg) phenotype. Even so, such iTreg phenotypes have not been characterized as to phenotype, function and/or migratory characteristics In one embodiment, the present invention contemplates a method to predict a phenotype and function of iTreg cells. In one embodiment, the iTreg cells may be produced by contacting non-Treg cells with a compound including but not limited to rapamycin, TGF-β and RA. In one embodiment, the rapa-iTreg comprises a different in vivo migratory pattern (e.g., homing capacity) than either TGF-β-iTreg or RA-iTreg. Although it is not necessary to understand the mechanism of an invention, it is believed that these differences in iTreg migratory patterns suggest their use in different diseases. In one embodiment, the iTreg cells may be produced by contacting non-Treg cells with a compound combination comprising TGF-β, RA and rapa, wherein the iTreg cells have a migratory pattern that is different from iTreg cells induced by any of the compounds alone.

A. Treg Cell Therapeutics

Regulatory T cell (Treg)-based therapies are widely regarded as promising treatment options for autoimmunity and transplant rejection. Currently, several therapies involving the use of ex vivo expanded Treg are being tested in clinical trials. However, there are significant barriers to ex vivo Treg-based therapies, such as difficulty in isolating pure populations of these rare cells and expanding them to sufficiently large numbers while maintaining their phenotype and function. Wieckiewicz et al., (2010) "T regulatory cells and the control of alloimmunity: From characterisation to clinical application" *Curr Opin Immunol* 22: 662-668; Riley et al., (2009) "Human T Regulatory Cell Therapy: Take a Billion or So and Call Me in the Morning" *Immunity* 30:656-665; Brusko et al., (2008) "Human regulatory T cells: Role in autoimmune disease and therapeutic opportunities" *Immunol Rev* 223: 371-390; Trzonkowski et al., (2009) "First-in-man clinical results of the treatment of patients with graft versus host disease with human ex vivo expanded CD4+CD25+CD127− T regulatory cells" *Clin Immunol* 133: 22-26; Brunstein et al., "Alternative donor transplantation after reduced intensity conditioning: results of parallel phase 2 trials using partially HLA-mismatched related bone marrow or unrelated double umbilical cord blood grafts" *Blood* 118: 282-288; and Safinia et al., (2010) "Adoptive regulatory T cell therapy: Challenges in clinical transplantation" *Curr Opin Organ Transplant* 15: 427-434.

One possible alternative to circumvent these issues is to generate adaptive or induced Treg (iTreg) from the patient's own naïve T cells either ex vivo or in vivo. Past reports have demonstrated that IL-2 and transforming growth factor β1 (TGF-β) can induce a Treg phenotype and functional characteristics in naïve T cells upon in vitro stimulation. Fu et al. (2004) "TGF-beta induces Foxp3+ T-regulatory cells from CD4+CD25—precursors" *American Journal of Transplantation* 4: 1614-1627; and Chen et al., (2003) "Conversion of Peripheral CD4+CD25− Naive T Cells to CD4+CD25+ Regulatory T Cells by TGF-beta Induction of Transcription Factor Foxp3" *Journal of Experimental Medicine* 198:1875-1886. However, TGF-β-induced Treg (TGFβ-iTreg) have been shown to be unstable in long term in vitro cultures and upon antigenic re-stimulation. Floess et al., (2007) "Epigenetic control of the foxp3 locus in regulatory T cells" *PLoS Biology* 5: 0169-0178. Additionally, the presence of inflammatory cytokines such as IL-6 can antagonize TGF-β-mediated induction of Treg, making the presence of such inflammatory mediators a potential impediment to inducing Treg in vivo at the site of the disease. Veldhoen et al., (2006) "TGF-beta in the context of an inflammatory cytokine milieu supports de novo differentiation of IL-17-producing T cells" *Immunity* 24: 179-189; and Bettelli et al., (2006) "Reciprocal developmental pathways for the generation of pathogenic effector TH17 and regulatory T cells" *Nature* 441: 235-238.

Numerous reports suggest that these problems can be overcome through the use of small molecules that work in concert with TGF-β to induce Treg. For example, all-trans retinoic acid (RA) is known to potently synergize with IL-2 and TGF-β to induce FoxP3 expression in naïve T cells and allows for induction of Treg even in the presence of inflammatory cytokines. Thorough characterization of the phenotype and function of RA-induced Treg (RA-iTreg) cells demonstrates superior suppressor activity and are more stable than TGFβ-iTreg cells. Nevertheless, RA-iTreg cells have a specific disadvantage in that they migrate primarily to the mucosal tissues in the gut, which might limit their use. Mucida et al., (2007) "Reciprocal TH17 and regulatory T cell differentiation mediated by retinoic acid" *Science* 317: 256-260; and Lu et al., (2011) "Characterization of Protective Human CD4+CD25+ FOXP3+ Regulatory T Cells Generated with IL-2, TGF-β and Retinoic Acid" *PLoS ONE* 5: 1-12; and Benson et al., (2007) "All-trans retinoic acid mediates enhanced T reg cell growth, differentiation, and gut homing in the face of high levels of co-stimulation" *Journal of Experimental Medicine* 204: 1765-1774.

Further, other evidence suggests additional disadvantages to RA-iTreg cells in that, depending on the immunological microenvironment, RA can induce inflammation rather than tolerance. DePaolo et al., (2011) "Co-adjuvant effects of retinoic acid and IL-15 induce inflammatory immunity to dietary antigens" *Nature* 471: 220-224. Also, RA has been shown to induce hypervitaminosis-A upon local administration, and hence it would be difficult to use this combination (cytokines+RA) to induce Treg in vivo. Jones D H, (1989) "The role and mechanism of action of 13-cis-retinoic acid in the treatment of severe (nodulocystic) acne" *Pharmacol Ther* 40: 91-106; and Barua et al., (1996) "Percutaneous absorption, excretion and metabolism of all-trans-retinoyl beta-glucuronide and of all-trans-retinoic acid in the rat" *Skin Pharmacol* 9: 17-26.

Another small molecule that synergizes with IL-2 and TGF-β to induce FoxP3 expression in naïve T cells is the serine/threonine protein kinase inhibitor rapamycin (rapa). Although it has been demonstrated that, like RA, rapa can induce Treg, even in the presence of IL-6. However, the phenotype and function of rapa-induced Treg (rapa-iTreg) has yet to be characterized. Kopf et al., (2007) "Rapamycin inhibits differentiation of Th17 cells and promotes generation of FoxP3+ T regulatory cells" *Int Immunopharmacol* 7: 1819-1824; Haxhinasto et al., (2008) "The AKT-mTOR axis regulates de novo differentiation of CD4+Foxp3+ cells" *J Exp Med* 205: 565-574; and Cobbold et al., (2009) "Infectious tolerance via the consumption of essential amino acids and mTOR signaling" *Proc Natl Acad Sci USA* 106: 12055-12060.

B. Small Molecule Enhancement of Treg Cell Proliferation

That data presented herein directly compares in vitro generated rapa-iTreg cell populations to TGFβ-iTreg, RA-iTreg and/or RA+rapa-iTreg cell populations. In many aspects, such as expression of canonical Treg markers and in vitro suppressive activity these different iTreg appear to be similar. However, notable differences are observed that have not been reported previously. For example, the expression of one of the canonical surface markers, FR4, was significantly greater on rapa-iTreg and RA+rapa-iTreg when compared to the RA-iTreg. Although it is not necessary to understand the mechanism of an invention, it is believed that expression of this folate receptor may allow for greater survival and long-term stability of Treg populations in the periphery.

Figure 1:
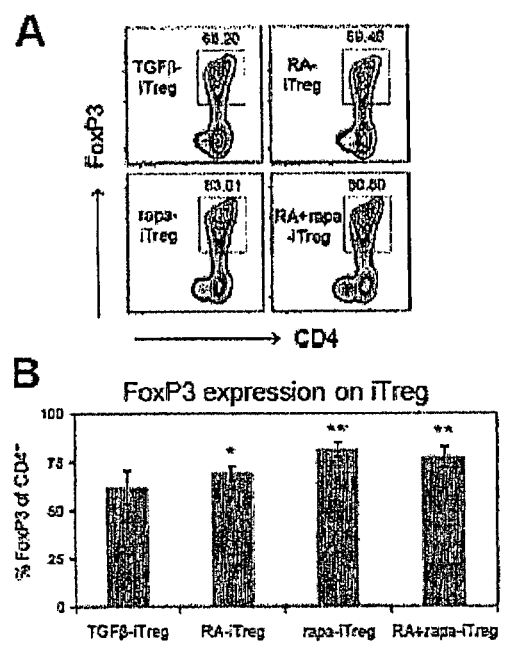
FIG. 1 presents exemplary data showing that retinoic acid (RA) and rapamycin (rapa) enhance TGFβ's capability to induce a Treg phenotype.
Figure 1:
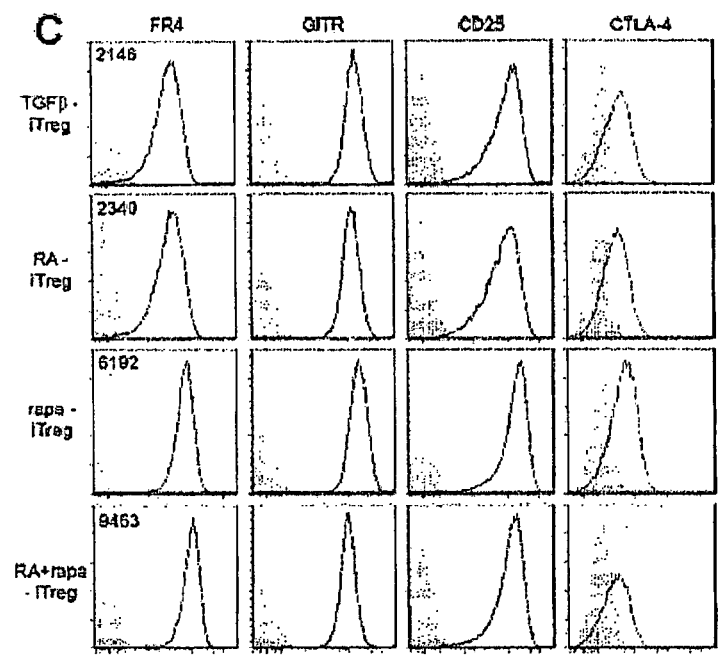

The data presented herein demonstrate that either RA or rapa enhance the ability of IL-2 and TGF-β to induce FoxP3 expression in naïve T cells. See, FIG. 1A, FIG. 1B, Table 1 and Table 2. The tabulated numbers below represent the percent of CD4+ that express FoxP3 under the indicated conditions.

TABLE 1

Rapamycin Percent Enhancement Of TGF-β Induction Of FoxP3 Expression

|  | TGF-β 0 ng/ml | TGF-β 0.1 ng/ml | TGF-β 1 ng/ml | TGF-β 5 ng/ml | TGF-β 20 ng/ml |
| --- | --- | --- | --- | --- | --- |
| Rapa 0 ng/ml | 0.52 | 0.61 | 2.82 | 18.16 | 53.26 |
| Rapa 1 ng/ml | 1.91 | 3.04 | 8.89 | 34.41 | 76.22 |
| Rapa 10 ng/ml | 3.45 | 5.31 | 14.48 | 51.08 | 78.27 |
| Rapa 100 ng/ml | 4.13 | 7.8 | 22.05 | 54.19 | 80.36 |

TABLE 2

Retinoic Acid Percent Enhancement Of TGF-β Induction Of FoxP3 Expression

|  | TGF-β 0 ng/ml | TGF-β 0.5 ng/ml | TGF-β 5 ng/ml | TGF-β 20 ng/ml |
| --- | --- | --- | --- | --- |
| RA 0 ng/ml | 1.69 | 8.08 | 28.52 | 27.42 |
| RA 0.1 ng/ml | 2.71 | 11.98 | 35.18 | 28.33 |
| RA 1 ng/ml | 2.64 | 10.5 | 44.71 | 42.25 |
| RA 10 ng/ml | 2.27 | 9.36 | 42.22 | 45.97 |
| RA 100 ng/ml | 2.23 | 10.01 | 50.71 | 43.43 |

Figure 2:
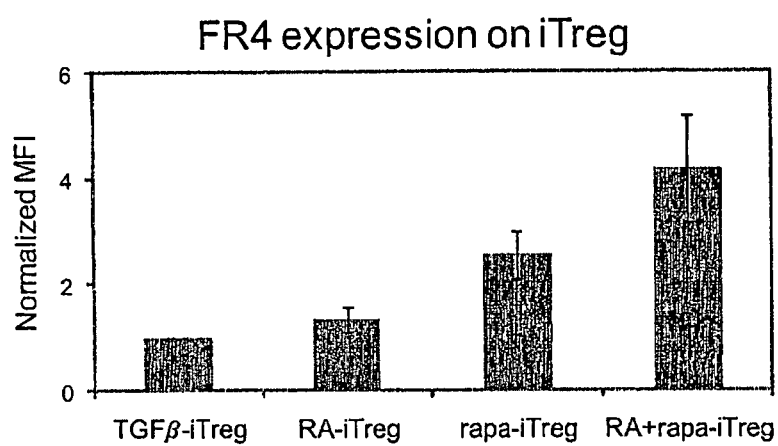
FIG. 2 presents exemplary data showing that rapamycin enhances induction of FR4 expression. Quantitative analysis of FR4 expression on iTreg generated under different conditions. Median fluorescence intensity (MFI) was determined after gating on the CD4+ FoxP3+ population. MFI values were normalized to TGFβ-iTreg FR4 expression. ** indicates $p<0.01$ when specified group was compared to the RA-iTreg group.
Figure 3:
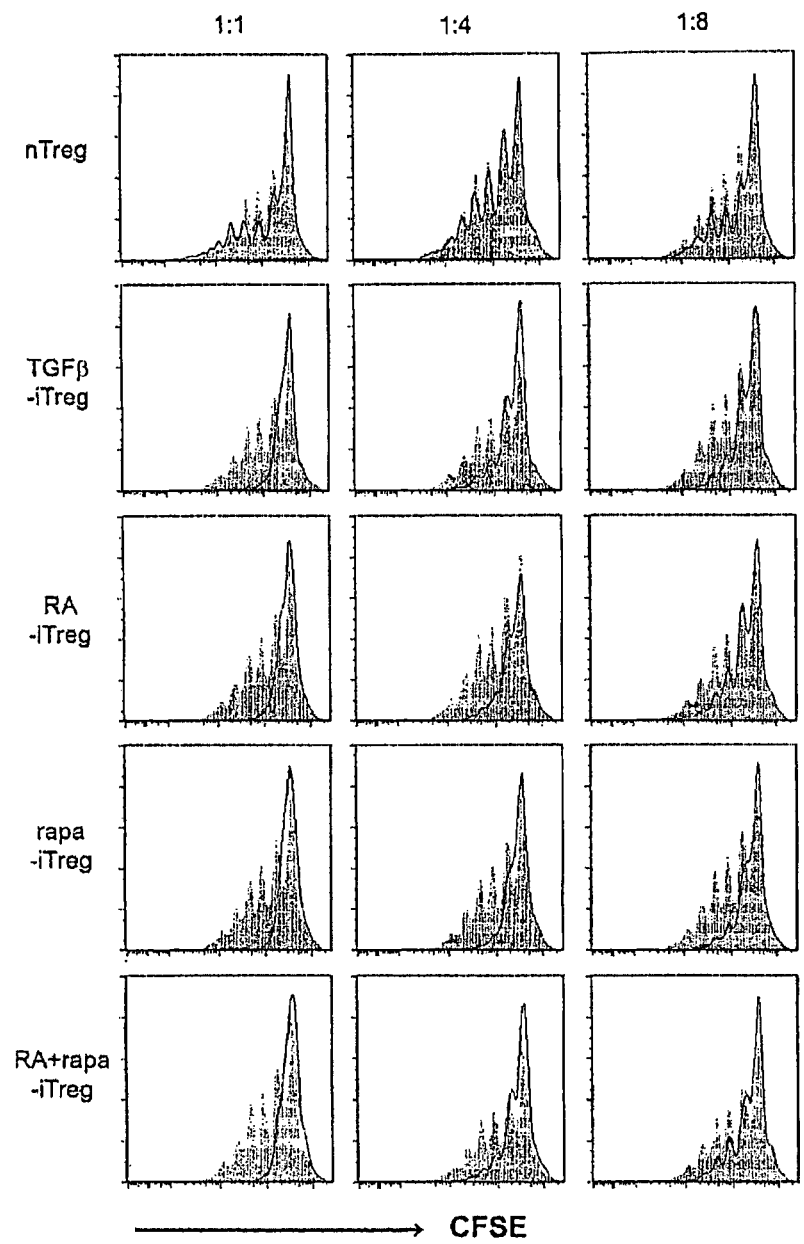
FIG. 3 presents exemplary data showing iTreg suppression of naïve T cell proliferation. Treg function was determined using a CFSE dilution assay. Filled histograms (grey) represent the proliferative capacity of naïve T cells only (in the presence of stimulation). Ratios indicate the ratio of Treg to naïve T cells. Plots are representative of at least 2 independent experiments.

The same effect was observed when cells are cultured in the presence of a combination of IL-2, TGF-β, RA and rapa. Cells cultured under all these different conditions also expressed canonical Treg markers, such as FR4, CTLA4, GITR and CD25, suggesting that these cells are induced Treg (iTreg). See, FIG. 1C. Interestingly, the expression level of FR4 was significantly greater in rapa-iTreg and RA+rapa-iTreg when compared to RA-iTreg. See, FIG. 2. FR4, along with CD25, has been identified as a marker that can help distinguish activated effector T cells from Treg. Yamaguchi et al., (2007) "Control of Immune Responses by Antigen-Specific Regulatory T Cells Expressing the Folate Receptor" *Immunity* 27: 145-159. In order to determine the functional capacity of iTreg, their ability to suppress autologous naïve T cell proliferation can be tested in vitro. For example, naïve T cells were isolated from CD45.1 mice and stained with CFSE were co-cultured with iTreg (generated from CD45.2 mice) in the presence of in vitro stimulation (αCD3/αCD28 labeled Dynal® beads). Naïve T cells were capable of robust proliferation when cultured in the absence of Treg but their proliferative capacity was decreased substantially (e.g., supressed) when cultured in the presence of iTreg generated under each of the different conditions examined. Additionally, the proliferative capacity of naïve T cells was restored as the ratio of naïve T cells to iTreg was increased. See, FIG. 3.

C. iTreg Stability Upon Re-Stimulation

Figure 4:
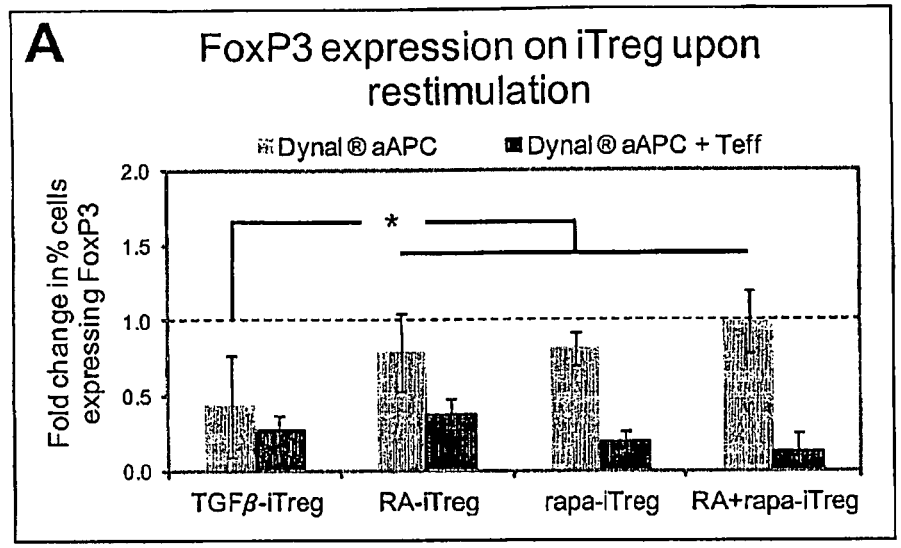
FIG. 4 presents exemplary data showing that the generation of iTreg cells in the presence of RA and/or rapa are more stable than TGFβ-iTreg cells in long-term in vitro cultures. Treg-inducing factors indicate the cytokines and/or small molecules used to generate the iTreg. Data are representative of 4 independent experiments. Fold change is expressed as the ratio between the % of FoxP3+ cells at the end of the re-stimulation cultures to the % of FoxP3+ cells at the beginning of the cultures. Dotted lines indicate normalized values of % of FoxP3+ cells at the beginning of the cultures.
Figure 4:
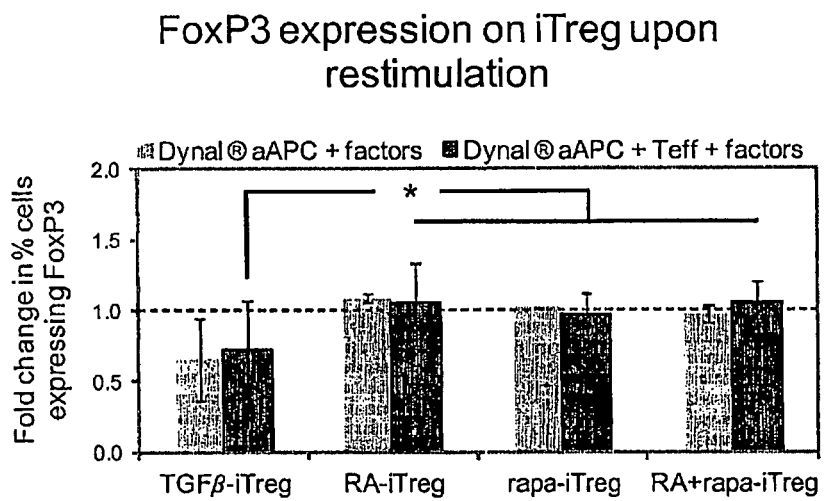

It has been demonstrated that, following long-term (>8 day) in vitro culture, there is a considerable reduction in the percentage of TGFβ-iTreg cells that express FoxP3. Floess et al., (2007) "Epigenetic control of the foxp3 locus in regulatory T cells" *PLoS Biology* 5: 0169-0178. To determine if the same was true of iTreg generated in the presence of RA and/or rapa, these iTreg populations were re-stimulated through TCR activation using Dynal® beads with IL-2 in either the absence or presence of effector T cells (Teff; generated by activating predominantly naïve T cells obtained from CD45.2 mice). Re-stimulation in the absence of Teff led to slightly reduced incidence of FoxP3+ cells among the iTreg, while the presence of Teff led to a marked decrease in FoxP3+ cells. See, FIG. 4A. When the Treg-inducing factors, IL-2, TGF-β and RA were present during re-stimulation the decrease in incidence of FoxP3+ cells was not observed. See, FIG. 4B. Regardless, a decrease in the percentage of cells expressing FoxP3 was observed in TGFβ-iTreg cultured under any of the aforementioned stimulatory conditions.

D. iTreg Migration Patterns

RA-iTreg cells have been reported to express surface markers such as CCR9 and CD103 that are specifically associated with migration to the mucosal tissues. Mucida et al., (2007) "Reciprocal TH17 and regulatory T cell differentiation mediated by retinoic acid" *Science* 317: 256-260; and Benson et al., (2007) "All-trans retinoic acid mediates enhanced T reg cell growth, differentiation, and gut homing in the face of high levels of co-stimulation" *Journal of Experimental Medicine* 204: 1765-1774. The expression of certain chemokine receptors and integrins on the surface of RA-iTreg, rapa-iTreg and RA+rapa-iTreg were observed to have differences. As demonstrated previously, expression of CCR9 and CD103 (surface molecules that direct migration of cells towards the small intestine lamina propria and the epithelium, respectively) was upregulated on RA-iTreg cells. Rapa-iTreg cells, however, did not express either of these surface proteins, but expressed the lymphoid organ-homing receptor CCR7 at significantly greater levels. This pattern of expression correlated with tissue-specific migration patterns. For example, rapa-iTreg cells demonstrate an in vivo lymphoid organ homing capacity, while RA-iTreg migrated primarily to the gut tissue. RA+rapa-iTreg also expressed higher levels of CCR7, but could be subdivided into 3 populations, where 35.66% cells were CCR9+ CD103+, 33.16% cells were CCR9+ CD103− and 22.14% cells were CCR9− CD103−. This distribution could suggest that cells affected by RA are not influenced by rapa and vice versa. It remains to be seen if such an expression pattern allows for the RA+rapa-iTreg to be more efficient at suppressing immune responses (due to their ability to migrate simultaneously to both mucosal tissues and lymphoid organs) in vivo, and if such an effect cannot be observed by using a mixture of RA-iTreg and rapa-iTreg.

Figure 5:
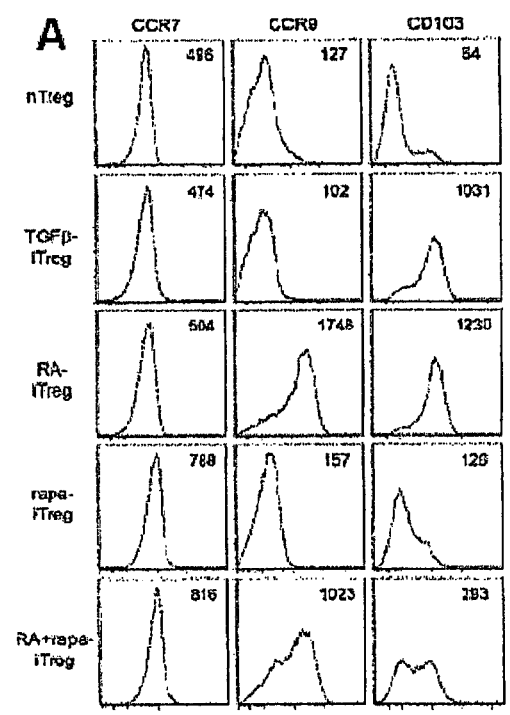
FIG. 5 present exemplary data showing a differential expression of migratory receptors on iTreg generated under different conditions.
Figure 5:
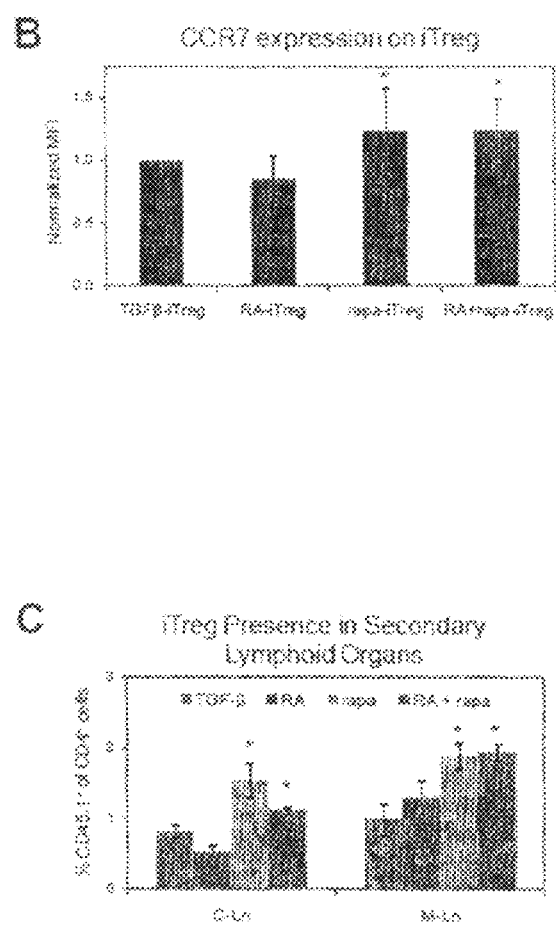
Figure 6:
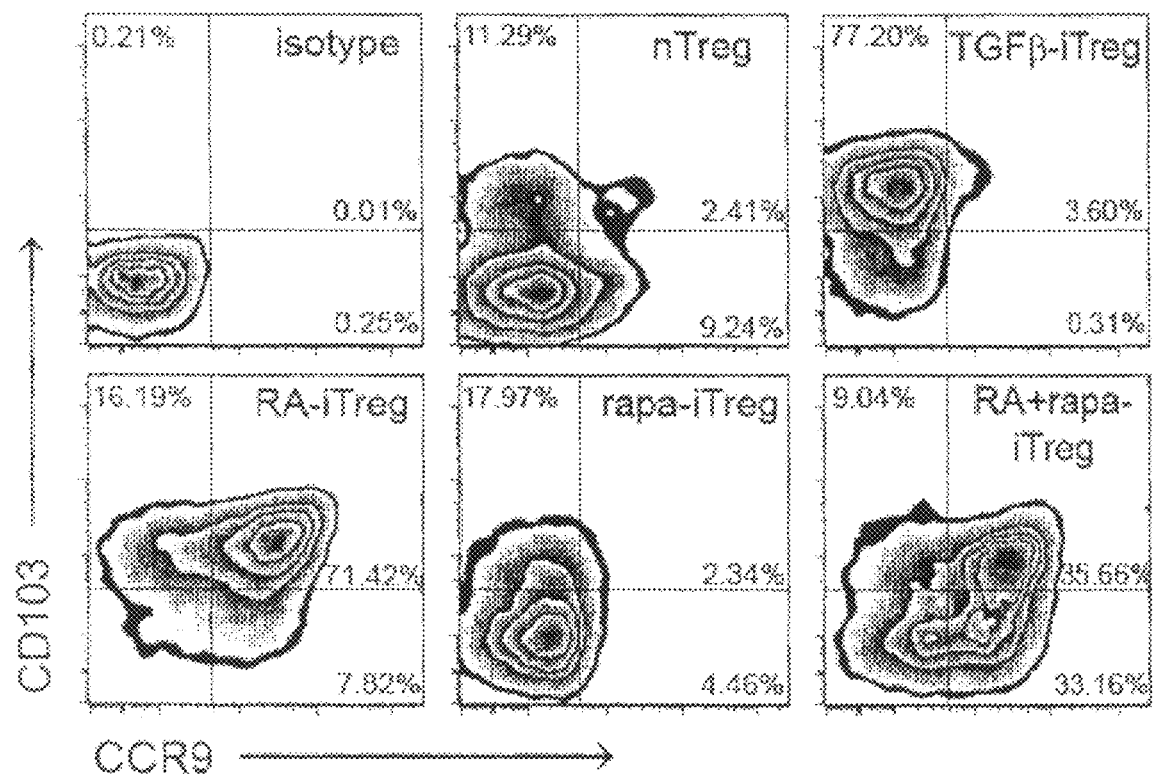
FIG. 6 presents exemplary data showing an analysis of surface molecules responsible for migration of T cells to peripheral tissues. Density plots show that RA induces expression of CCR9 on iTreg, while rapa reduces expression of CD 103 and CCR9. The RA+rapa-iTreg appear to comprise of two distinct populations of cells; one that is CCR9+CD103+ and another that is CCR9−CD103−.
Figure 7:
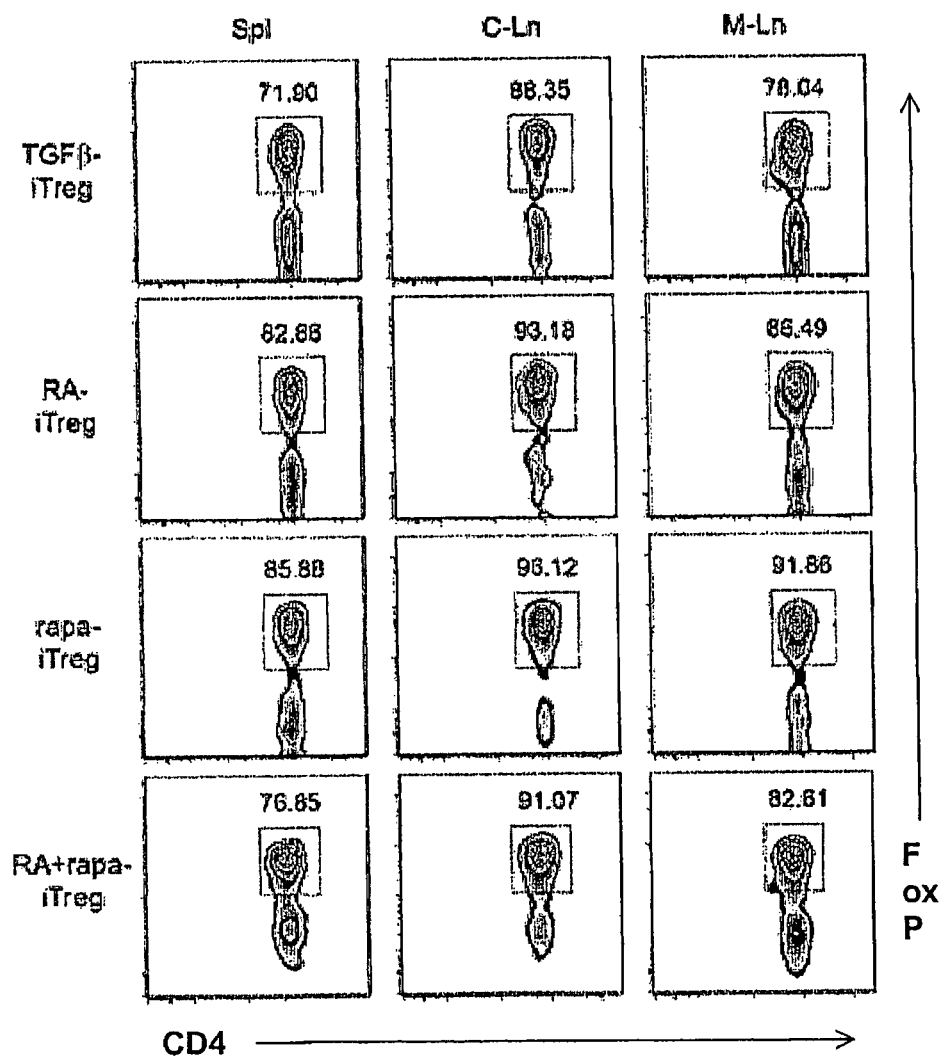
FIG. 7 presents exemplary data showing various iTreg cell populations that maintain FoxP3 expression following injection in mice maintained under homeostatic conditions. Analysis of FoxP3 expression on CD45.1+ cells 3 days following their adoptive transfer into wild-type CD45.2+ mice. Spl indicates spleen, C-Ln indicated cervical lymph nodes and M-Ln indicates mesenteric lymph nodes.

The data presented herein show that rapa-iTreg did not express either CCR9 or CD103 but did express significantly higher levels of CCR7 when compared to RA-iTreg. See, FIG. 5A and FIG. 5B. The RA+rapa-iTreg cells, which also expressed significantly elevated levels of CCR7, appear to contain two distinct iTreg populations: i) a CCR9+ CD 103+ population; and ii) a CCR9– CD 103– population. See FIG. 6. To determine if the expression of these receptors would determine in vivo homing, rapa-, RA-, TBGβ- and RA+rapa iTreg cell populations generated from CD45.1 mice were adoptively transferred to healthy CD45.2 mice maintained under homeostatic conditions. Three days following adoptive transfer, a significantly greater number of rapa-iTreg cells and RA+rapa-iTreg cells were present in the cervical and mesenteric lymph nodes when compared to the presence of TGFβ-iTreg cells and RA-iTreg cells. See, FIG. 5C. Additionally, all adoptively transferred iTreg populations maintained their FoxP3 expression. See, FIG. 7.

In vivo migration patterns of the various adoptively transferred iTreg cell populations were monitored by non-invasive imaging over an extended time-period (~10 days). Following adoptive transfer of luminescent iTreg populations, RA-iTreg cell populations and rapa-iTreg cell populations migrate primarily to the gut and lymphoid tissues, respectively, within 3 days and remain at these sites for over 10 days. These data also reflect that RA+rapa-iTreg cell populations migrate to both the secondary lymphoid organs and the gut, although there were considerably greater numbers of cells in the gut tissue. This observation may be explained by a possible imaging of mesenteric lymph nodes among with the gut tissue. See, FIG. 8A and FIG. 8B, respectively.

Although RA- and/or rapa-induced Treg were more stable when compared to conventional TGFβ-iTreg upon re-stimulation, RA and rapa-iTreg cells tended to lose their FoxP3 expression in the presence of stimulation and Teff (an in vitro mimic of inflammatory conditions). This loss of FoxP3 expression was limited to the presence of Teff since in the presence of mature dendritic cells, such an effect was not observed. Nevertheless, the inflammatory effect of Teff was negated in the presence of an immunosuppressive milieu (such as the combination of IL-2, TGF-β, and RA or rapa) and iTreg maintained their FoxP3 expression even after incubation with Teff. This suggests that the use of Treg induced in the presence of RA and/or rapa might be limited to situations where an immunosuppressive milieu can be established; for example, using low dose immunosuppressive regimens, or controlled release formulations for immunomodulatory agents. Jhunjhunwala et al., (2009) "Delivery of rapamycin to dendritic cells using degradable microparticles" *J Control Rel* 133: 191-197. Furthermore, recently it has been suggested that the methylation patterns on the Foxp3 gene locus are a good determinant of long-term Treg stability. It remains to be determined if these iTreg differ in this aspect.

Given the difficulties and cost associated with cellular therapies, a system capable of inducing Treg in vivo would be ideally suited to treating autoimmunity and transplant rejection. To this end, it would be necessary to use formulations that deliver a combination of Treg-inducing factors in a local and sustained fashion in vivo, which can be achieved using controlled release formulations that have been developed in the past. Thomas et al., (2004) "Microparticulate Formulations for the Controlled Release of Interleukin-2" *J Pharm Sci* 93: 1100-1109; and DeFail et al., (2006) "Controlled release of bioactive TGF-β from microspheres embedded within biodegradable hydrogels" *Biomaterials* 27: 1579-1585. The preferred combination of factors to be used in vivo might be IL-2, TGF-β, and rapa, as (i) rapa is currently approved for use clinically, (ii) rapa has the ability to suppress a variety of immune functions apart from inducing Treg, and (iii) rapa might be safer than RA, given the latter's ability to induce hypervitaminosis A.

III. Conventional Controlled Release Formulations

Several drug delivery systems are known that provide for a roughly uniform and controllable rate of release. A variety of different media are described below that are useful in creating drug delivery systems.

Microparticles generally refer to the general categories comprising liposomes, nanoparticles, microspheres, nanospheres, microcapsules, and nanocapsules. Preferably, some microparticles contemplated by the present invention comprise poly(lactide-co-glycolide), aliphatic polyesters including, but not limited to, poly-glycolic acid and poly-lactic acid, hyaluronic acid, modified polysacchrides, chitosan, cellulose, dextran, polyurethanes, polyacrylic acids, psuedo-poly(amino acids), polyhydroxybutrate-related copolymers, polyanhydrides, polymethylmethacrylate, poly(ethylene oxide), lecithin and phospholipids.

Microspheres and microcapsules are useful due to their ability to maintain a generally uniform distribution, provide stable controlled compound release and are economical to produce and dispense. Microspheres are obtainable commercially (Prolease®, Alkerme's: Cambridge, Mass.). For example, a freeze dried medium comprising at least one therapeutic agent is homogenized in a suitable solvent and sprayed to manufacture microspheres in the range of 20 to 90 μm. Techniques are then followed that maintain sustained release integrity during phases of purification, encapsulation and storage. Scott et al., *Improving Protein Therapeutics With Sustained Release Formulations*, Nature Biotechnology, Volume 16:153-157 (1998).

Modification of the microsphere composition by the use of biodegradable polymers can provide an ability to control the rate of therapeutic agent release. Miller et al., *Degradation Rates of Oral Resorbable Implants {Polylactates and Polyglycolates: Rate Modification and Changes in PLA/PGA Copolymer Ratios*, J. Biomed. Mater. Res., Vol. II:711-719 (1977).

Alternatively, a sustained or controlled release microsphere preparation is prepared using an in-water drying method, where an organic solvent solution of a biodegradable polymer metal salt is first prepared. Subsequently, a dissolved or dispersed medium of a therapeutic agent is added to the biodegradable polymer metal salt solution. The weight ratio of a therapeutic agent to the biodegradable polymer metal salt may for example be about 1:100000 to about 1:1, preferably about 1:20000 to about 1:500 and more preferably about 1:10000 to about 1:500. Next, the organic solvent solution containing the biodegradable polymer metal salt and therapeutic agent is poured into an aqueous phase to prepare an oil/water emulsion. The solvent in the oil phase is then evaporated off to provide microspheres. Finally, these microspheres are then recovered, washed and lyophilized. Thereafter, the microspheres may be heated under reduced pressure to remove the residual water and organic solvent.

Other methods useful in producing microspheres that are compatible with a biodegradable polymer metal salt and therapeutic agent mixture are: i) phase separation during a gradual addition of a coacervating agent; ii) an in-water drying method or phase separation method, where an antiflocculant is added to prevent particle agglomeration and iii) by a spray-drying method.

Controlled release microcapsules may be produced by using known encapsulation techniques such as centrifugal extrusion, pan coating and air suspension. Such microspheres and/or microcapsules can be engineered to achieve desired release rates. For example, Oliosphere® (Macromed) is a controlled release microsphere system. These particular microsphere's are available in uniform sizes ranging between 5-500 μm and composed of biocompatible and biodegradable polymers. Specific polymer compositions of a microsphere can control the therapeutic agent release rate such that custom-designed microspheres are possible, including effective management of the burst effect. ProMaxx® (Epic Therapeutics, Inc.) is a protein-matrix delivery system. The system is aqueous in nature and is adaptable to standard pharmaceutical delivery models. In particular, ProMaxx® are bioerodible protein microspheres that deliver both small and macromolecular drugs, and may be customized regarding both microsphere size and desired release characteristics.

A microsphere or microparticle may comprise a pH sensitive encapsulation material that is stable at a pH less than the pH of the internal mesentery. The typical range in the internal mesentery is pH 7.6 to pH 7.2. Consequently, the microcapsules should be maintained at a pH of less than 7. However, if pH variability is expected, the pH sensitive material can be selected based on the different pH criteria needed for the dissolution of the microcapsules. The encapsulated compound, therefore, will be selected for the pH environment in which dissolution is desired and stored in a pH preselected to maintain stability. Examples of pH sensitive material useful as encapsulants are Eudragit® L-100 or S-100 (Rohm GMBH), hydroxypropyl methylcellulose phthalate, hydroxypropyl methylcellulose acetate succinate, polyvinyl acetate phthalate, cellulose acetate phthalate, and cellulose acetate trimellitate. In one embodiment, lipids comprise the inner coating of the microcapsules. In these compositions, these lipids may be, but are not limited to, partial esters of fatty acids and hexitiol anhydrides, and edible fats such as triglycerides. Lew C. W., Controlled-Release pH Sensitive Capsule And Adhesive System And Method. U.S. Pat. No. 5,364,634 (herein incorporated by reference).

Microparticles may also comprise a gelatin, or other polymeric cation having a similar charge density to gelatin (i.e., poly-L-lysine) and is used as a complex to form a primary microparticle. A primary microparticle is produced as a mixture of the following composition: i) Gelatin (60 bloom, type A from porcine skin), ii) chondroitin 4-sulfate (0.005%-0.1%), iii) glutaraldehyde (25%, grade 1), and iv) 1-ethyl-3-(3-dimethylaminopropyl)-carbodiimide hydrochloride (EDC hydrochloride), and ultra-pure sucrose (Sigma Chemical Co., St. Louis, Mo.). The source of gelatin is not thought to be critical; it can be from bovine, porcine, human, or other animal source. Typically, the polymeric cation is between 19,000-30,000 daltons. Chondroitin sulfate is then added to the complex with sodium sulfate, or ethanol as a coacervation agent.

IV. Predicting Controlled Release Profiles

In some embodiments, the present invention contemplates compositions providing a predictable controlled release of compounds to induce a Treg phenotype (e.g., determined by the expression of canonical Treg markers and migratory surface markers). In one embodiment, the induced Treg phenotype includes but is not limited to TGFβ-iTreg, RA-iTreg and rapa-iTreg. In one embodiment, a combination of IL-2, TGF-β and rapa induces Treg with greater functional stability when compared to TGFβ-iTreg. In one embodiment, a rapa-iTreg cell comprises a lymphoid migration pattern. In one embodiment, a RA-iTreg cell comprises an intestinal migratory pattern.

In one embodiment, the present invention contemplates compositions and methods for the development and testing of controlled release formulations for Treg induction compounds (e.g., IL-2, TGF-β and rapamycin) having predictable independent and differential release profiles. In other words, the release profile for each component in the formulation is released with a custom-tailored predetermined kinetic and temporal pattern. Rothstein et al., "A simple model framework for the prediction of controlled release from bulk eroding polymer matrices" *J Mater Chem* (2008) 18:1873-1880; and Rothstein et al., "A unified mathematical model for the prediction of controlled release from surface and bulk eroding polymer matrices" *Biomaterials* (2009) 30:1657-1664. As is shown herein, the specific composition of a microparticle can be determined, in advance, that results in the differential release profiles of each component. Although it is not necessary to understand the mechanism of an invention, it is believed that the interaction of the differential release profiles from these microparticle populations result in the creation of an iTreg cell population that has a predicted migration pattern and/or tissue target. The data presented herein show that these various microparticle formulations (e.g., generic designation as "Factor" MP formulations) are capable of Treg cell population induction in vitro using either mouse or human cells. Also demonstrated is that the "Factor" MP-induced Treg maintain their proliferative capacity and functional ability in vitro and express phenotypic surface markers that are consistent with soluble factor-induced Treg.

Controlled release formulations for the individual regulatory T cell inducing factors (IL-2, TGF-β and rapamycin) have been previously reported. However, the improvements described herein demonstrate that the controlled release of a combination of individual regulatory T cell inducing factors can generate mouse and human Treg cells having predictable migration patterns. In one embodiment, the present invention contemplates compositions comprising synthetic formulations (e.g., custom designed microparticles) capable of inducing Treg cell populations that have specific migratory patterns and/or target tissues.

The absence of regulatory T cells (Treg) may be involved in a wide variety of disorders including but not limited to, autoimmunity, dermatitis, periodontitis and/or transplant rejection. Logically, one potential treatment option for these disorders would be to increase local Treg numbers. For example, enhancing local numbers of Treg cells might be achieved through in situ Treg expansion or induction. Current methods for in vivo Treg expansion rely on biologic therapies, which are not Treg-specific and are associated with many adverse side-effects.

The data presented herein describe the development and in vitro testing of a Treg-inducing synthetic formulation comprising a specific polymer composition that provides a vehicle for predictable controlled release of IL-2, TGF-β and rapamycin. While combinations of IL-2, TGF-β and rapamycin have been reported to be co-administered previously, the combination therapy was not delivered where each compound followed a pre-determined controlled release profile that results in an iTreg cell population have a predictable migratory pattern and/or target tissue. In one embodiment, IL-2, TGF-β and rapamycin are released in pre-determined controlled release profiles over an approximate three-to-four (3-4) week period. In one embodiment, IL2-TGFβ-rapa-iTreg cell populations produced by predetermined controlled release profiles express iTreg phenotype canonical makers. Functionally, these IL2-TGFβ-rapa iTreg cell populations suppress naïve T cell proliferation and T cell function at levels similar to soluble factor induced Treg as well as naturally occurring Treg. These release formulations are also capable of inducing FoxP3+ Treg in human cells in vitro. These data suggest that pre-determined controlled release formulations of IL-2, TGF-β and rapa can expand a functional Treg population in vivo that has a predictable migratory pattern and therapeutic effect.

A. Controlled Release Microparticle Characterization

The data presented herein use IL-2MP, TGFβMP, and rapaMP formulations that were prepared under similar conditions comprising the polymer (RG502H) having a viscosity of 0.16-0.24 dl/g. See, Example V. Scanning electron micrographs (FIG. 1, left panel) show that individual particles are spherical and confirm the volume average size distributions (IL-2MP=25.5±7.5 µm; TGFβMP=16.7±6.3 µm; rapaMP=16.7±6.4 µm; errors indicate standard deviation from the mean for each particle set). FIG. 9, left panel. Additionally, the images reveal that IL-2MP have slightly porous exterior surfaces. These particles were specifically formulated to be porous by altering osmotic pressures between the inner emulsion and the outside aqueous phase during microparticle preparation. It was predicted that this composition would comprise a high initial release burst followed by a continuous release. Further, a predicted linear release of TGF-β was observed from the TGFβMP population after a ~2 week lag phase, and a predicted continuous release of rapamycing from the rapaMP population. See, FIG. 9, right panel.

B. Treg Cell Induction by Predicted Microparticle Release Profiles

Soluble IL-2, TGF-β and rapa factors were used as positive controls to the "FactorMP" inductions because previous reports have shown successful Treg cell population induction. [24-25]. The data show that some embodiments of the "Factor" MP formulations as contemplated by the present invention had a similar efficacy as soluble factors during in vitro Treg induction, as measured by FoxP3 expression. See, FIG. 10A and FIG. 10B. (FIGS. 2A and 2B). Although it is not necessary to understand the mechanism of an invention, it is believed that the degradable polymer-based formulations as designed herein release T cell inducing factors reliably to create functional iTreg cell populations. In addition, the "Factor" MPs were capable of inducing Treg cell populations by releasing equivalent (~2-3 ng IL-2 and/or ~2-10 ng rapa), or reduced (~0.2-0.4 ng of TGF-β) total amounts of the factors over 4 days of culture. The CFSE data also suggests that the iTreg cells underwent a robust proliferation. See, FIG. 10A.

C. Phenotype and Function of "Factor" MP-iTreg Cells

Treg are known to express a variety of characteristic surface proteins in addition to FoxP3. Consequently, the iTreg cell populations induced by "Factor" MP populations described herein were typed for three other canonical Treg surface markers: CD25, FR-4 and GITR. CD25 is believed to be a high-affinity IL-2 receptor, which may increase sensitivity to IL-2 and is believed involved in Treg proliferation. FR-4 is classified as a folate receptor, and may participate in folic acid sensing and uptake, processes that can prolong Treg survival. GITR is a surface receptor that has been suggested to play a role in Treg survival and suppression.

"Factor" MP-iTreg cell populations expressed each of these surface markers at levels equivalent to Treg cells induced by soluble factors. See, FIG. 11A. Although it is not necessary to understand the mechanism of an invention, it is believed that the expression of these surface proteins, along with FoxP3, suggests that these cells are Treg cells, but the cells may, or may not, have a suppressive capability.

FactorMP-iTreg cell populations were assayed as to whether these cells retained a capability to suppress naïve T cell proliferation using an in vitro co-culture system. Collison et al., "In vitro Treg suppression assays" *Methods Mol Biol*. (2011) 707:21-37. The data showed that "Factor" MP-iTreg cell populations did retain T cell proliferation suppressive capabilities similar to Treg induced by soluble factors and natural Treg. See, FIG. 11B.

D. "Factor" MP iTreg Human Cells

Human T cells isolated from PBMC have been reported to be induced into a Treg phenotype using soluble factors such as IL-2, TGF-β and rapa. Hippen et al., "Generation and large-scale expansion of human inducible regulatory T cells that suppress graft-versus-host disease" *Am J Transplant* (2011) 11:1148-1157; and Kawamoto et al., "Transforming growth factor beta 1 (TGF-beta1) and rapamycin synergize to effectively suppress human T cell responses via upregulation of FoxP3+ Tregs" *Transpl Immunol*. (2010) 23:28-33. Although it is not necessary to understand the mechanism of an invention, it is believed that a clinical application of some "Factor" MP formulation embodiments would benefit from a determination of whether these formulations were capable of inducing Treg cell populations from human T cells. The data presented herein was collected from human T cells cultured in the presence of soluble Treg inducing factors or embodiments of "Factor" MP formulations as described herein. The data show that "Factor" MP formulations were equally capable of inducing Treg when compared to the soluble factors and released either an equivalent (1-10 ng/ml rapa) or reduced (2-4 ng/ml TGF-β) amounts of factors as determined by FoxP3 expression. See, FIG. 12 and FIG. 12B.

E. Controlled Release of Vasoactive Intestinal Peptide

Vasoactive intestinal peptide (VIP) is a 28-amino acid neuropeptide originally isolated from the intestine that is believed to have numerous biological functions. For example, VIP has been reported to down-regulate a variety of pro-inflammatory responses and up-regulate anti-inflammatory responses, and has been administered as a therapeutic mouse model in experimental collagen-induced arthritis, sepsis, Crohn's disease, and experimental autoimmune encephalomyelitis (EAE). Although it is not necessary to understand the mechanism of an invention, it is believed that VIP may shift the Th1-Th2 balance in the favor of Th2 by promoting Th2-type cytokine production and, at the same time, by inhibiting Th1 development and responses. Delgado et al. "Vasoactive intestinal peptide prevents experimental arthritis by downregulating both autoimmune and inflammatory components of the disease" *Nat. Med.* (2001) 7:563-568; Fernandez-Martin et al., "Vasoactive intestinal peptide induces regulatory T cells during experimental autoimmune encephalomyelitis" *Eur. J. Immunol.* (2006) 36:318-326; and Gonzalez-Rey et al., "Vasoactive intestinal peptide and regulatory T-cell induction: a new mechanism and therapeutic potential for immune homeostasis" *Trends in Molecular Medicine* (2007) 13:241-251.

More recently, new mechanisms have been proposed that identify the role of VIP in inducing and recruiting regulatory T (Treg) cells that may play a role in maintaining immune homeostasis. See, FIG. 13. Both natural and inducible regulatory T cells are believed involved involved in immune tolerance and regulation. For example, natural Treg cells develop in the thymus as CD4+CD25+FoxP3+ Tregs, and expand in the periphery. Pozo et al., "Tuning immune tolerance with vasoactive intestinal peptide: A new therapeutic approach for immune disorders" *Peptides* (2007) 28:1833-1846. Alternatively, the so-called inducible Treg cells can be generated from CD4+CD25− and CD8+CD25− naïve T cells under certain stimulation patterns. Treg induction by VIP may occur in at least two different pathways. One alternative comprises VIP directly activating naïve CD4+CD25− T cells to have a regulatory phenotype. A second alternative comprises VIP steering immature dendritic cells (DCs) toward a tolerogenic phenotype. Such tolerogenic DCs can then induce CD4+ and CD8+ naïve T cells toward a regulatory phenotype (inducible Tregs). It has also been reported that VIP can induce tolerogenic dendritic cells to produce CCL22, a chemokine known involved in the recruitment of regulatory T cells. Delgado et al., "VIP/PACAP preferentially attract Th2 effectors through differential regulation of chemokine production by dendritic cells" *FASEB J* (2004) 18:1453-1455.

One known difficulty in attempting to use VIP-based therapies is the short half-life of VIP in the body. One approach to address this challenge has focused on attempts to develop VIP analogs which deliver the same therapeutic benefits as VIP but are metabolically stable. Misaka et al., "Inhalable powder formulation of a stabilized vasoactive intestinal peptide (VIP) derivative: Anti-inflammatory effect in experimental asthmatic rats" *Peptides* (2010) 31:72-78. However, VIP analogues only extend the half-life to 4 hours and the liposomes offer only short-term release, releasing 77-87% of encapsulated VIP within the first two hours in vitro. Wernig et al., "Depot formulation of vasoactive intestinal peptide by protamine-based biodegradable nanoparticles" *J of Controlled Release* (2008) 130:192-198. Another approach might involve protecting the VIP by encapsulation into sterically stabled liposomes. Such liposomal particles would be expected to deliver a longer lasting release profile and are therefore a more promising approach to a VIP-based therapy.

The data presented herein describes an alternative method of quantifying VIP release using microparticles composed of 12.6 kDA PGLA. The released VIP was detected using a commercially available VIP Enzyme Immunoassay kit (Phoenix Pharmaceuticals). Dentritic cell (DC) cultures were tested to determine the bioactivity of VIP released from these microparticles. The results suggest that VIP microparticles have a significant therapeutic potential as a treatment for periodontitis.

In one embodiment, the present invention contemplates a composition comprising a VIPMP formulation having a polymer composition predicted by mathematical analysis to provide a pre-determined release profile.

A. VIP Release from VIPMPs Having Pre-Determined Release Profiles

Controlled release of VIP from VIPMPs made in accordance with Examples XI and XII was measured over a 60 day period and evaluated for both a predicted linear release profile and a predicted multi-bolus release profile.

Release assays were performed in triplicate for six batches of VIP microparticles, but only two sets were evaluated using the ELISA plates. The remaining samples were stored at −80° C. for future evaluation. Four microparticle sets contained particles of pure polymer weight: 4.2 kDA, 12.6 kDa with and without PEG, and 100 kDa. Predictive model calculations generated proposed ratios of microparticles with different polymer molecular weights (10.6% of the 4.2 kDa, 31.9% of the 12.6 kDa without PEG, and 57.5% of the 100 kDa polymer) that predicted a linear release for a period of approximately 50 days Rothstein et al., "A simple model framework for the prediction of controlled release from bulk eroding polymer matrices" *J of Mater. Chem.* (2007) 18:1873-1880. This algorithmic model further suggested that when 4.2 kDa, 12.6 kDa with PEG, and 55 kDa polymers were mixed in equal amounts, the resultant microparticle would be expected to have an extended multi-bolus release profile.

The VIP release profiles for both the linear and multi-bolus VIPMPs showed initial bursts followed by an extended release over the period of 60 days. As would be expected from the algorithm prediction, showed a secondary burst around day 15 and a possible start of a tertiary burst at day 45. Further, the multi-bolus group released about twice as much VIP as compared to the linear profile VIPMP. The linear VIPMPs released much slower than the multi-bolus VIPMPs and at day 5, release of VIP from the linear VIPMPs began releasing in a near-linear fashion. See. FIG. 14A. A comparison of the observed release and the model prediction of the linear VIPMPs is presented that ignores the initial burst occurring during the first five days of release profile. See, FIG. 14B.

With the exception of the initial burst, the computer model successfully predicted the polymer ratio necessary to achieve a near-linear release of VIP for a period of 50 days. Although it is not necessary to understand the mechanism of an invention, it is believed that that the release of VIP may be delayed due to ionic interactions of VIP with the PLGA polymer. VIP has an exceptionally high isoelectric point of 11.8, meaning that at pH of 7, the peptide has a net positive charge. Since the polymer is negatively charged, the VIP could aggregate with the polymer. It appeared that the VIP did not finish releasing from both the linear and multi-bolus groups, although the model predicted complete release by day 50.

B. VIP Bioactivity Assays

To show that VIP microparticles released bioactive VIP, dentritic cell (DC) cultures and chemotaxis studies were performed. Three separate DC cultures with 24 individual wells were completed in accordance with Example XIII. Both GM-CSF and IL-4 were used to culture the cells in the first two DC cell cultures, but for the third DC culture, the IL-4 was omitted to reduce its possible interference in steering immune cells toward a tolerogenic phenotype. Chemotaxis studies of CD4+ T-cells were performed and the percent of FoxP3+ T-cells which flowed through the transwells for each group was evaluated using flow. The data is presented as a normalized percent of FoxP3+ cells which were recruited by the DCs for the first DC when both IL-4 and GM-CSF were used to culture the DC precursors and when GM-CSF was used alone in the last DC culture. The DCs treated with soluble VIP or releasates from VIP microparticles recruited a higher percentage of FoxP3+ cells than DCs that only received LPS or releasates from blank particles. See, FIG. 15.

DCs cultured in the absence of IL-4 showed similar trends in the recruitment of regulatory T cells, suggesting VIP itself (not IL-4) is responsible for CCL22 induction. When the DC culture was repeated with the absence of IL-4 and addition of 5×GM-CSF, flow cytometry indicated slightly different trends. The DCs treated with LPS alone, soluble VIP, and releasates from VIP microparticles recruited the same percentage of FoxP3+ cells. The DCs treated with releasates from the blank microparticle groups recruited less FoxP3+ cells than the other groups. The distinction between the VIP microparticle group and the blank microparticle group was increased when no IL-4 was used.

In the in vitro DC cultures, a higher percentage of FoxP3+ regulatory T-cells after chemotaxis indicated that the DCs produced more CCL22, a chemokine known to be involved in regulatory T cell recruitment. The released VIP appeared to be bioactive since the DCs treated with releasates from VIP microparticles showed higher percentage recruitment of FoxP3+ cells than those treated with blank releasates for all three experiments. Studies have shown that CCL22 production of DC cells does not increase as significantly after treatment with soluble VIP. Delgado et al., "VIP/PACAP preferentially attract Th2 effectors through differential regulation of chemokine production by dendritic cells" (2004) *FASEB J* 18:1453-1455. As IL-4 has been suggested to skew DC differentiation, IL-4 was omitted from the fourth DC culture in attempt to yield greater distinction between groups in percent FoxP3+ cell recruitment. Robinson et al., "Chapter 17. Generation of Murine Bone-Marrow-Derive Dendritic Cells" (2001) *Dendritic Cell Protocols* 191-98. While there was a greater difference between the blank microparticles and VIPMPs of the DC culture without IL-4, the LPS control, soluble VIP, and VIP microparticle groups all appeared to show similar trends.

C. In Vivo Imaging of VIPMP Periodontal Treatment

A micro-computerized tomographic analysis images of mouse alveolar bone used to determine bone loss in mice following administration of blank MPs, CCL22MPs, and VIPMPs. The data distinguishes the cementoenamal junction (CEJ) as a focal point on which to quantitate bone loss data using either a linear measurement or a volumetric measurement technique. FIG. 16. Park et al., "Three Dimensional Micro-Computed Tomographic Imaging of Alveolar Bone in Experimental Bone Loss or Repair" (2007) *J. Periodontol.* (2007) 78:273-281.

Figure 17:

Micro-CT analysis has not yet been reported as a technique to evaluate alveolar bone loss in mice having periodontitis treated with VIP microparticles. However, micro-CT analysis has been performed on mice having periodontitis which received CCL22MP treatment. FIG. 17.

V. Predicting "Factor" MP Formulation Release Profiles

In some embodiments, the present invention contemplates improving upon methods comprising increasing a Treg cell:Teff cell ratio. For example, is has been reported that a combination of soluble T cell inducing factors such as IL-2, TGF-β and rapamycin establish an environment that favors an increase in this ratio. Haxhinasto et al., "The AKT-mTOR axis regulates de novo differentiation of CD4+Foxp3+ cells" *J Exp Med* (2008) 205565-574; Kopf et al., "Rapamycin inhibits differentiation of Th17 cells and promotes generation of FoxP3+ T regulatory cells" *Int Immunopharmacol* (2007) 7:1819-1824; Cobbold et al., "Infectious tolerance via the consumption of essential amino acids and mTOR signaling" *Proc Natl Acad Sci USA* (2009) 106:12055-12060; and Thomson et al., "Immunoregulatory functions of mTOR inhibition" *Nat Rev Immunol.* (2009) 9:324-337. In one embodiment, the present invention contemplates a method to create an improved immunosuppressive, Treg-inducing environment by providing "FactorMP" formulations that provide a predictable and sustained release of T cell inducing factors at a local site. In one embodiment, the "FactorMP" formulation comprises a polymer (e.g., PLGA). Although it is not necessary to understand the mechanism of an invention, it is believed that these formulations are prepared in accordance with a pre-fabrication mathematical analysis that creates a unique microparticle composition that results in a pre-determined release profile tailored for the induction and proliferation of specific Treg cell populations.

For example, IL-2 is believed involved in Treg cell survival, and it has been suggested that high initial IL-2 concentrations might improve Treg cell proliferation and resist apoptosis. Shevach, "CD4+ CD25+ suppressor T cells: more questions than answers" *Nat Rev Immunol.* (2002) 2:389-400; and von Boehmer, "Dynamics of suppressor T cells: in vivo veritas", (2003) 198:845-849. In one embodiment, a mathematical calculation predicted a specific microparticle polymer composition comprising a slightly porous IL-2MP that provided a high initial IL-2 release burst, followed by a slow continuous IL-2 release over an approximate five (5) week time frame. In one embodiment, a mathematical calculation predicted a specific and novel microparticle polymer composition comprising a two (2) week lag period that is followed by a continuous TGF-β linear release formulation for TGF-β for approximately three (3) weeks. Although it is not necessary to understand the mechanism of an invention, it is believed that the initial two (2) week lag phase can be mathematically predicted by calculations describing the ionic interactions between TGF-β and PLGA. It is further believed that these ionic interactions could be a result of the high isoelectric point (pI) of TGF-β and the relatively low pH conditions inside the microparticles. In one embodiment, a mathematical calculation predicted a specific and novel microparticle polymer composition comprising an immediate continuous TGF-β linear release wherein the polymer is pre-incubated the TGFβMP in culture media for approximately 18-22 days. In one embodiment, a mathematical calculation predicted a specific and novel microparticle polymer composition that continuously releases rapamycin over a 2-3 week time frame.

In one embodiment, the present invention contemplates a composition comprising a plurality of "Factor" MP formulations. Although it is not necessary to understand the mechanism of an invention, it is believed that such "Factor" MP formulations are as effective as soluble factors that induce Treg from naïve T cells. In one embodiment, the "Factor" MP iTreg cells provide a robust Treg cell proliferation, express canonical Treg surface markers, and suppress naïve T cell proliferation. Further, it was observed that Treg induction and proliferation occurred even when the cells were in contact with microparticles, suggesting that the microparticles do not have adverse on these cells. In one embodiment, "Factor MP" formulations induce human T cells into an iTreg cell population. In one embodiment, the human-iTreg comprises a high expression of FoxP3 and is capable of proliferation (data not shown).

In one embodiment, the present invention contemplates method comprising administering "Factor" MP populations in vivo for treating medical conditions such as transplant rejection and/or autoimmunity mediated by a local Treg cell population induction.

VI. Mathematical Prediction of Microparticle Release Profiles

In some embodiments, the present invention contemplates using a broadly applicable model for predicting controlled release that eliminates the need for exploratory, in vitro experiments during the design of new biodegradable matrix-based therapeutics. For example, a simple mathematical model can predict the release of many different types of agents from bulk eroding polymer matrices without regression. Such models comprise deterministically calculating the magnitude of the initial burst and the duration of the lag phase (time before Fickian release) by making predictions based upon easily measured or commonly known parameters. This model describes the release of water-soluble agents that are discretely encapsulated in bulk eroding, polymer matrices and that dissolve rapidly, relative to the time scale of release. In addition to using specific equations, the model includes two correlations that enable predictions with knowledge of just five parameters, all commonly known or easily measured prior to release. These parameters are microsphere radius ($R_p$), occlusion radius ($R_{occ}$), polymer degradation rate ($kC_w$), polymer initial molecular weight ($M_{wo}$), and agent molecular weight ($M_{wA}$). A regression to a desired dosing schedule generates a set of matrix design parameters to guide the fabrication of a matching controlled release therapeutic.

Briefly, the operation of the predictive algorithm can be described as follows. Consider an initially uniform matrix of known geometry comprised of a biodegradable polymer, such as a polyester or polyanhydride, and with randomly distributed entrapped release agent (e.g. drug of concentration $C_{Ao}$), loaded below its percolation threshold (such that agent remains discrete) to ensure matrix mediated release. This agent can either be dispersed as crystals (such as in the case of uniformly loaded systems, e.g. single emulsion-based particulates) or housed as a solution in occlusions (e.g. double emulsion-based particulates). At time zero, an aqueous reservoir begins to hydrate the matrix, a process which happens quickly for the bulk eroding polymers matrices considered herein. As the matrix hydrates, encapsulated agent adjacent to the matrix surface (with a direct pathway for egress) diffuses into the reservoir in a phase typically dubbed "the initial burst"). The relative size of the occlusion ($R_{occ}$) occupied by the encapsulated agent is proportional to the magnitude of the initial burst. As the initial burst release commences, degradation of the polymer begins, increasing chain mobility and effectively leading to the formation of pores in the polymer matrix. Although a number of mechanisms have been proposed for this heterogeneous degradation profile, one hypothesis, which has been reinforced by experimental data, is based upon regions of varying amorphicity and crystallinity. It is believed that (as shown using scanning electron microscopy). These pores appear to be essential for subsequent release.

With the cumulative growth and coalescence of these pores, agents are able to diffuse towards the surface of a polymer matrix that would otherwise be too dense to allow their passage. Thus, a pore is defined as a region of polymer matrix with an average molecular weight low enough to allow the release of encapsulated agent. (This is in contrast to the occlusion, which is defined as a region occupied by dissolved or solid agent, marked by the absence of polymer matrix.). Further, the molecular weight associated with release may vary for each encapsulated agent type (small molecule, peptide, protein, etc.), leading to a size-dependent restriction for agent egress.

With a size-dependent restriction on egress established, the degradation controlled release of any encapsulated agent can only occur when the following four conditions are satisfied. 1) The release agent must be present in the polymer matrix. 2) A pore must encompass the release agent. 3) That release agent must be able to diffuse through the encompassing pore. 4) The pore must grow and coalesce with others to create a pathway for diffusion to the surface.

Agent concentration within a matrix (such a microsphere, rod, or thin film) can be calculated from Fick's second law (Equation 1) for any point in time (t) or space (r), provided that the agent is not generated or consumed in any reactions while within the matrix.

$$\frac{\partial C_A}{\partial t} = \nabla(D_{eff} \nabla C_A) \tag{1}$$

where $D_{eff}$ is an effective diffusivity term. Integrating $C_A/C_{ao}$ over the entire matrix volume yields the cumulative fraction of agent retained in the matrix (P(t)) (Equation 2).

$$P(t)=V^{-}\int C_A/C_{Ao}dV \tag{2}$$

In turn, the cumulative fraction of agent released (R(t)), a metric commonly used to document formulation performance, is simply (Equation 3):

$$R(t)=1-P(t) \tag{3}$$

At the center point, line, or plane of the matrix (r=0) symmetry conditions are defined such that $dC_A/dr=0$. At the matrix surface ($r=R_p$) perfect sink conditions are specified. A boundary also exists at a depth of $R_{occ}$ in from the matrix surface ($r=R_p-R_{occ}$) where continuity conditions are defined. In the subdomain from $R_p$ to $R_p-R_{occ}$ (terminating one occlusion radius in from the particle surface), agent is subject to the initial release, such that $D_{eff}$ is simply a constant (D), reflecting the movement of agent through the hydrated occlusions abutting the matrix surface. In the subdomain from 0 to $R_p-R_{occ}$, agent is subject to pore-dependent release, such that $D_{eff}=D\varepsilon$ where D is the diffusivity of the agent through the porous matrix and E is the matrix porosity.

For a system of like matrices, such as microspheres or sections in a thin film, that degrade randomly and heterogeneously, the accessible matrix porosity is simply a function of time as a discrete pore has, on average, an equal probability of forming at any position in the polymer matrix. Hence, the time until pore formation can be calculated from the degradation of the polymer matrix, as any differential volume containing a pore would have a lower average molecular weight than its initial value. Assuming that the polymer degradation rate is normally distributed, the induction time for pore formation will also follow a normal distribution. As this pore formation is cumulative, the timedependent matrix porosity (3(t)) can be described with a cumulative normal distribution function (Equation 4).

$$\varepsilon(t) = \frac{1}{2}\left[\operatorname{erf}\left(\frac{t-\tau}{\sqrt{2\sigma^2}}\right)+1\right] \tag{4}$$

In this equation, $\tau$ is the mean time for pore formation and $\sigma^2$ is the variance in time required to form pores.

Calculating the cumulative normal induction time distribution ($\varepsilon(t)$) requires values for $\tau$ and $\sigma^2$. For polymers that obey a first order degradation rate expression, the mean time for pore formation ($\tau$) can be determined as follows:

$$\tau = \frac{-1}{kC_w}\ln\left|\frac{M_{wr}}{M_{wo}}\right|$$

where $kC_w$ is the average pseudo-first order degradation rate constant for the given polymer type, $M_{wo}$ is the initial molecular weight of the polymer, and we define $M_{wr}$ as the average polymer molecular weight in a differential volume of matrix that permits the diffusion of the encapsulated agent. For blended polymer matrices, the value for $\tau$ was calculated by averaging the results obtained from Equation 5 for each component.

It is reasonable to believe that the matrix molecular weight at release ($M_{wr}$), which dictates how much degradation is required before release can occur, would vary depending on the size of the encapsulated agent. Macromolecules or larger agents can only diffuse through a section of matrix if it is almost entirely free of insoluble polymer chains. Hence the $M_{wr}$ for such agents is considered the polymer solubility molecular weight (e.g., 668 Da for 50:50 PLGA). As agent size decreases (as indicated by $M_{wA}$), however, egress can occur through more intact sections of polymer matrix (higher $M_{wr}$), as less free space is needed to allow their passage.

The distribution of polymer degradation rates ($kC_w(n)$) attributed to matrix crystallinity is needed to calculate the variance ($\sigma^2$) in the induction time distribution for Animals Six-eight week-old C57BL/6 and B6.SJL-Ptprca/BoyAiTac (CD45.1) mice were purchased from Taconic and used within two months of delivery. B6(Cg)-Tyrc-2J/J (albino C57BL/6 mice) were purchased from The Jackson Laboratory. C57BL/6.Luc+ mice were a kind gift from Dr. Stephen Thorne (Dept. of Surgery, University of Pittsburgh). All animals were maintained under specific pathogen-free conditions.

Materials

Mouse CD4 negative isolation kit, αCD3/αCD28-labeled beads (aAPC Dynal®) and Vybrant CFDA-SE cell tracer kit were from Invitrogen Corporation (Carlsbad, Calif., USA). Recombinant mouse IL-2 (R&D systems, Minneapolis, Minn., USA), recombinant human TGF-β1 (CHO cell-derived, PeproTech, Rocky Hills, N.J., USA), all-trans-retinoic acid (Sigma, St. Louis, Mo., USA), and rapamycin was from LC labs (Woburn, Mass., USA). The following antibodies were purchased from eBioscience (San Diego, Calif., USA): CD4 (L3T4), FoxP3 (FJK-16s), CD45.1 (A20), CD103 (2E7), CD25 (PC61.5), glucocorticoid-induced TNFR-related protein—GITR(DTA-1), FR4 (eBio12A5), CCR7 (4B12) and CCR9 (eBioCW-1.2). Anti-cytotoxic T-lymphocyte antigen 4-CTLA-4 (UC10-4B9) was from BioLegend (San Diego, Calif., USA). Anti-PE microbeads were obtained from Miltenyi Biotec (Auburn, Calif., USA).

T Cell Isolation

Spleen and lymph nodes were dissected from mice, and single cell suspensions were prepared using mechanical digestion. Following RBC lysis, CD4+ cell isolation was performed using the CD4 negative isolation kit (Invitrogen) as per the manufacturer's instructions. To enrich for CD25− cells, CD4+ cells were incubated with anti-mouse CD25-PE antibody (eBioscience) followed by addition of anti-PE microbeads (Miltenyi). Bead-bound CD25+ cells were isolated by passing cells through a magnetic column. Unbound CD4+ CD25− cells were separated and used to induce Treg.

Treg Induction

Freshly-isolated naïve CD4+ CD25− cells were cultured with aAPC Dynal® beads at a 2:1 (dynal:cell) ratio in the presence of 10 ng/ml IL-2, 20 ng/ml TGF-β1 and/or 3 ng/ml (10 nM) RA and/or 10 ng/ml rapa. To obtain effector T cells (Teff), CD4+ CD25− cells were cultured with aAPC Dynal® beads and 10 ng/ml IL-2 only. Cell cultures were maintained for 4 days, and cells separated subsequently from the magnetic Dynal® beads. To determine induction of Treg phenotype, FoxP3 staining and flow cytometry (BD-LSRII) were performed at the end of the 4-day culture period as per the manufacturer's instructions (eBioscience).

Example II

In Vitro Suppression Assay

Freshly-isolated naïve CD4+ CD45.1+ cells were stained with Carboxyfluorescein diacetate succinimidyl ester (CFSE; Invitrogen, as per the manufacturer's instructions) and co-cultured with autologous induced Treg (generated as described above) at different ratios in 96-well plates. The number of naïve CD4+ CD45.1+ cells was always 50,000 cells/well. For stimulation, 25,000 aAPC Dynal® beads per well were used (2:1, naïve cell:Dynal ratio). Co-cultures were maintained for 4 days, followed by staining for flow cytomtery.

Example III

In Vitro iTreg Stability Testing iTreg cells generated under different conditions and effector T cells (Teff, generated by stimulating naïve T cells in the presence of IL-2 only) were obtained from 4-day cultures and rested in 10 ng/ml IL-2 for 2 days. Thereafter the cells were cultured along with aAPC Dynal® beads as stimulators: (i) for Dynal® only (no Teff and no factors) group, 100,000 iTreg were cultured with 200,000 Dynal® beads along with 10 ng/ml IL-2; (ii) for Dynal®+Teff (no factors) group, 50,000 iTreg cells were cultured with 50,000 Teff cells and 100,000 Dynal® beads along with 10 ng/ml IL-2; (iii) for Dynal®+factors (no Teff) group, 100,000 iTreg cells were cultured with 200,000 Dynal® beads and respective factors at the concentrations described above; (iv) for Dynal®+Teff+ factors group, 50,000 iTreg cells were cultured with 50,000 Teff cells and 100,000 Dynal® beads and respective factors. Re-stimulation experiments were carried out for 4 days and cells were then stained and analyzed by flow cytometry.

Example IV

In Vivo Migration Experiments iTreg cells generated from naïve CD45.1+ CD4+ CD25− cells were injected into CD45.2 mice at a concentration of $2 \times 10^6$ cells in 200 µl PBS per animal (lateral tail vein). Three days following injection, mice were euthanized and the spleen, cervical lymph nodes and mesenteric lymph nodes collected. Single cell suspensions from each of these tissues were prepared, stained for different markers and analyzed by flow cytometry.

For in vivo live animal imaging experiments, iTreg cells were generated from C57BL/6.Luc+ mice and injected into albino C57BL/6 mice at a concentration of $1 \times 10^6$ cells in 200 µl PBS per animal (lateral tail vein). At defined time-points, mice were injected (i.p.) with 200 µl luciferin (30 mg/ml) and imaged using the IVIS 200 (Xenogen VivoVision, Caliper Life Sciences, Hopkinton, Mass., USA). Luminescent images were analyzed and quantified using Igor Pro Living Image® 2.60.1 (Caliper Life Sciences).

Example V

Controlled Release Microparticle Preparation

IL-2 and TGF-β microparticles (IL-2MP and TGFβMP, respectively) were prepared using the double emulsion-evaporation technique. Thomas et al., "Microparticulate formulations for the controlled release of interleukin-2" *J Pharm Sci.* (2004) 93:1100-1109; and DeFail et al., "Controlled release of bioactive TGF-beta 1 from microspheres embedded within biodegradable hydrogels" *Biomaterials* (2006) 27:1579-1585.

The IL-2MP population was prepared under the following conditions: i) Five µg of recombinant (r) mouse IL-2 (R&D Systems Minneapolis, Minn.) was mixed with 2 mg of BSA and 5 mM NaCl in 200 µl of de-ionized water; ii) this solution was added to 4 ml of dichloromethane containing 200 mg of poly lactic-co-glycolic acid (PLGA; RG502H, Boehringer Ingelheim Chemicals Inc., Petersburg, Va.); iii) the mixture was agitated using a sonicator (Vibra-Cell, Newton, Conn.) at 25% amplitude for 10 sec, creating the primary emulsion; iv) the primary emulsion was then mixed with 60 ml of 2% polyvinyl-alcohol (PVA, MW ~25,000, 98% hydrolyzed; Polysciences) under homogenization (L4RT-A, Silverson, procured through Fisher Scientific) at 3000 rpm for 1 min, creating a double emulsion; v) the double-emulsion was then added to 80 ml of 1% PVA, and left for 3 hr spinning at 600 rpm thereby creating the microparticles; and vi) the microparticles were centrifuged (200 g, 5 min, 4° C.), washed 4 times in de-ionized water, and lyophilized (Virtis Benchtop K freeze dryer, Gardiner, N.Y.; operating at 80 mTorr).

The TGFβMP population was prepared under the following conditions: i) one μg of r-human TGF-β (CHO cell-derived, PeproTech, Rocky Hill, N.J.) was mixed with 10 mg D-mannitol, 1 mg of BSA, and 15 mM NaCl in 200 μl of de-ionized water; ii) this solution was added to 4 ml of dichloromethane containing 200 mg of PLGA (RG502H), and the mixture agitated using a sonicator at 25% amplitude for 10 sec, creating a primary emulsion; iii) this primary emulsion was then mixed with 60 ml of 2% PVA (containing 125 mM NaCl) under homogenization at 3000 rpm for 1 min, creating a double emulsion; iv) the double emulsion was then added to 80 ml of 1% PVA (containing 125 mM NaCl), and left for 3 hr spinning at 600 rpm thereby creating the microparticles; and v) the microparticles were centrifuged (200 g, 5 min, 4° C.), washed 4 times in de-ionized water, and lyophilized.

The rapaMP population was prepared using a single emulsion-evaporation technique. Jhunjhunwala et al., "Delivery of rapamycin to dendritic cells using degradable microparticles" *J Control Release* (2009) 133:191-197; and Eghtesad et al., "Rapamycin ameliorates dystrophic phenotype in mdx mouse skeletal muscle" *Mol Med* (2011). Briefly; i) 1 mg of rapa (LC labs, Woburn, Mass.) dissolved in DMSO was mixed with 4 ml of dichloromethane containing 200 mg of PLGA (RG502H); ii) the solution was mixed with 60 ml of 2% PVA under homogenization at 3000 rpm for 1 min thereby creating a microparticle emulsion; iii) the microparticle emulsion was then added to 80 ml of 1% PVA and left for 3 hr spinning at 600 rpm to create the microparticles: and iv) the microparticles were centrifuged (200 g, 5 min, 4° C.), washed 4 times in de-ionized water, and lyophilized.

Example VI

In Vitro Microparticle Release Assays

Release assays were conducted by incubating a suspension of particles; (i) 10 mg in 1 ml of media for IL-2MP and TGFβMP, and (ii) 10 mg in 1 ml of PBS (containing 0.2% Tween-80) for rapaMP, on a roto-shaker at 37° C. At regular time intervals, particle suspensions were centrifuged (250 g, 5 min), the supernatant removed, and the particles re-suspended in 1 ml of appropriate solution. The amount of each cytokine in the supernatant was measured using a cytokine-specific ELISA (R&D systems, Minneapolis, Minn.), and the amount of rapa was measured using spectrophotometry (absorbance at 278 nm).

Example VII

Mouse T Cell Isolation

Six-eight week old C57B1/6 (B6) and B6.SJL-Ptprca/BoyAiTac (CD45.1) were purchased from Taconic and used within two months. All animals were maintained under specific pathogen free conditions. Experiments were conducted in accordance with the National Institutes of Health Guide for Care and Use for Laboratory Animals and under Institutional Animal Care and Use Committee-approved protocols.

Spleen and lymph nodes were dissected from B6 or CD45.1 mice. Following mechanical digestion, the tissue suspension was passed through a 70 μm nylon filter to obtain a single cell suspension of leukocytes. Predominantly naïve CD4+ T cells (>90% pure) were isolated from this suspension with a CD4+ T cell negative isolation kit (Invitrogen, Carlsbad, Calif.) as per the manufacturer's instructions. These purified CD4+ T cells were used in cell culture and suppression assays.

Example VIII

Induction of Mouse Regulatory T Cells (Treg)

For Treg cell population induction, naïve T cells were cultured either in direct contact with "Factor" MPs in 96-well round bottom cell culture plates, or separated from "Factor" MPs by permeable transwell inserts (HTS Transwell®-96, 0.4 μm pore size; Corning, Lowell, Mass.). Dynabeads® mouse T-activator CD3/CD28 beads (Dynabeads®; Invitrogen, Carlsbad, Calif.) were used to activate the T cells at a 2:1 (beads:T cells) ratio. Cultures were then maintained for at least 4 days.

For cultures grown in the presence of soluble T cell induction factors, the following concentrations of factors were used: 10 ng/ml IL-2, 5 ng/ml TGF-β and 10 ng/ml rapa (corresponds to a total amount of 2 ng IL-2, 1 ng TGF-β and 2 ng rapa). For cultures grown tin the presence of the "Factor" MP populations the following amounts were added to 200 μl of cell culture media: i) 2 mg TGFβMP; ii) 0.5 mg IL-2MP; and iii) ~0.01-0.05 mg rapaMP.

The phenotypes of the induced T cells was determined by staining with anti-CD4 (L3T4), anti-FoxP3 (FJK-16s), anti-CD25 (PC61.5), anti-glucocorticoid-induced TNFR-induced protein (GITR; DTA-1), anti-folate receptor-4 (FR4; eBio12A5) (antibodies from eBiosciences, San Diego, Calif.) and anti-cytotoxic T-lymphocyte antigen 4 (CTLA4; UC10-4B9, from Biolegend, San Diego, Calif.). To determine iTreg proliferation, naïve T cells were stained with carboxyfluorescein diacetate succinimidyl ester cell tracer (CFSE; Invitrogen, Carlsbad, Calif.) prior to activation with Dynabeads®. Stained cells were then analyzed on a BD-LSRII flow cytometer.

Example IX

Suppression Assays

Freshly-isolated naïve CD4+CD45.1+ T cells were stained with CFSE (Invitrogen, as per the manufacturer's instructions) and co-cultured with iTreg cells generated in accordance with Example VIII at different ratios in 96-well plates. The number of naïve CD4+ CD45.1+ cells was kept constant at 50,000 cells/well. For stimulation, 50,000 Dynabeads® were used per well. Co-cultures were carried out for 4 days, after which cells were stained for flow cytometry.

Example X

Human T Cell Culture

CD4+ T cells were isolated from human PBMC using the CD4 negative isolation kit (Miltenyi Biotec, Auburn, Calif.).

Cells (500,000) were cultured in 0.5 ml of media (with serum) in the presence of human T cell activation beads (anti-CD2, anti-CD3 and anti-CD28 coated beads, Miltenyi Biotec, Auburn, Calif.). Cell culture media was supplemented with additional factors or FactorMP at the following concentrations: 500 U/ml recombinant-human IL-2, 10 ng/ml TGF-β, 2 ng/ml rapa, 8 mg/ml of TGFμMP, and/or 0.02 mg/ml of rapaMP. Following 4 days of culture, cells were collected, stained and Treg induction analyzed by flow cytometry. Soluble IL-2 was used in all of these cultures instead of IL-2MP, as IL-2MP encapsulated mouse rIL-2 and not the human protein.

Example XI

VIPMP Formulations

VIP microparticles (VIPMPs) were prepared following calculations using a model guided fabrication protocol. Rothstein et al., "A simple model framework for the prediction of controlled release from bulk eroding polymer matrices" *J of Mater. Chem.* (2008) 18:1873-1880. The mathematical algorithm of the computer model suggests specific polymer ratios to achieve desired release kinetic profiles. Separate batches of microparticles were fabricated which could then be combined in model-specified ratios to obtain complex release behaviors.

Three batches were comprised of individual PLGA polymer molecular weights using 4.2 kDa polymer, RG502H PLGA polymer (12.6 kDa), and RG505 polymer (55 kDa). Additionally, a fourth batch was fabricated with the 12.6 kDa polymer which contained poly(ethylene glycol) (PEG) at approximately $4\times10^{-4}$ mM in the inner aqueous phase. The inner aqueous phases of all VIPMPs comprises approximately 1250 μg/ml VIP. Unloaded (or "blank") sets of particles were also fabricated for each batch.

Example XII

VIPMP Release Assays

Sample of released VIP were collected for each of the four batches of VIPMPs made in accordance with Example XI. VIP release was also measured for two sets of VIPMPs with varying polymer ratios determined by a computer model that predicted a linear and multi-bolus release profile, respectively.

For the predicted linear release profile VIPMPs, the computer model suggested a microparticle composition comprising ratios of 10.6% of the 4.2 kDa polymer, 31.9% of the 12.6 kDa polymer (without PEG), and 57.5% of the 100 kDa polymer.

For multi-bolus release profile VIPMPs the computer model suggested a microparticle composition comprising ratios of 33.3% each of the 4.2 kDa, 12.6 kDa (with PEG), and 100 kDa polymers. Additionally, six sets of blank microparticles for each group were also collected at each time-point. Release assays in physiological buffered saline (PBS) conducted for each set of microparticles. Ten milligrams of blank microparticles or VIPMPs and 1 mL of either media or PBS were incubated at 37° C. Vials were centrifuged at 2000 rpm, and 800 μL of supernatant was removed and saved at −80° C., and replaced with fresh PBS for each time point. VIP concentration was determined using a VIP EIA kit purchased from Phoenix Pharmaceuticals. Samples were diluted up to 10×.

Example XIII

VIP Bioactivity Assays

Dendritic cells were isolated from murine bone marrow and cultured following standard procedures.

In the first two experiments, both GM-CSF and IL-4 were added to DC media (modified RPMI 1640) of bone marrow cell cultures during media changes on Days 0, 3 and 6. In the third experiment, the IL-4 was purposely omitted and GM-CSF was added in 5× concentration. On Day 6, CD11c+ DC cells were isolated using MACS cell sorting beads and plated in a 24-well plate at 100,000 cells/well. Five different groups of four wells each were analyzed and received treatment. An immature DC control group did not receive LPS. A mature DC control group received only LPS. Three different groups were matured with LPS and received different concentrations of either soluble VIP or releasates of VIP microparticles or blank microparticles (using the 12.6 kDa polymer). Soluble VIP was added to the third group in concentration of $2.5\times10^{-8}$ M. Ten milligrams of microparticles were first incubated for 4-6 hours in media and 250 of releasates were added to each well. After treatment, the DCs were incubated for approximately 18 hours. Prior to the CD4+ T cell chemotaxis study, the 24-well plate was centrifuge and the media was removed. The cells were then starved with 600 μl, PBS+1% BSA and incubated for one hour.

Example IVX

CD4+ Cell Isolation and Chemotaxis

CD4+ T-cells were isolated from the spleen and lymph nodes of a mouse using Dynal® beads following a standard protocol. Transwells were added to the 24-well plate containing the DCs and 100 μL of PBS and 1% BSA containing 500,000 CD4+ cells were added to each transwell and incubated for two hours. T Cells that flowed through were analyzed for FoxP3+ expression using flow cytometry.

The invention claimed is:

1. A method for inducing folate receptor 4 expressing regulatory T-cells at a tissue of a subject having an inflammatory disorder, wherein the tissue exhibits at least one symptom of the inflammatory disorder, comprising:
administering a formulation locally to said target the tissue, wherein the formulation comprises a first sustained release microparticle population comprising transforming growth factor beta, a second sustained release microparticle population comprising rapamycin, and a third sustained release microparticle population comprising IL-2;
wherein the transforming growth factor beta, the rapamycin, and IL-2 are released at the tissue to induce the folate receptor 4 expressing regulatory T-cells.

2. The method of claim 1, wherein one or more microparticle population comprises a polymer, and wherein the weight ratio of a therapeutic agent to the polymer is between about 1:100000 and about 1:1.

3. The method of claim 2, wherein the weight ratio of a therapeutic agent to the polymer is between about 1:20000 and about 1:500.

4. The method of claim 3, wherein the weight ratio of a therapeutic agent to the polymer is between about 1:10000 and about 1:500.

5. The method of claim 1, wherein the IL-2 microparticle has an initial release burst.

* * * * *

UNITED STATES PATENT AND TRADEMARK OFFICE
CERTIFICATE OF CORRECTION

PATENT NO. : 10,765,634 B2
APPLICATION NO. : 14/372977
DATED : September 8, 2020
INVENTOR(S) : Steven R. Little et al.

Page 1 of 1

It is certified that error appears in the above-identified patent and that said Letters Patent is hereby corrected as shown below:

In the Specification

In Column 10, Line 16, before the "DETAILED DESCRIPTION", please insert the following paragraph:
-- Figure 17 presents in vivo imaging of VIPMP periodontal treatment. --

Signed and Sealed this
Third Day of November, 2020

Andrei Iancu
*Director of the United States Patent and Trademark Office*